US008617617B2

(12) United States Patent  
Giordano et al.

(10) Patent No.: US 8,617,617 B2  
(45) Date of Patent: Dec. 31, 2013

(54) METHODS AND KITS FOR CO-ADMINISTRATION OF NUTRITIONAL SUPPLEMENTS

(75) Inventors: John A. Giordano, West Orange, NJ (US); Charles J. Balzer, Lavalette, NJ (US)

(73) Assignee: Everett Laboratories, Inc., Chatham, NJ (US)

(*) Notice: Subject to any disclaimer, the term of this patent is extended or adjusted under 35 U.S.C. 154(b) by 1734 days.

(21) Appl. No.: 11/643,886

(22) Filed: Dec. 22, 2006

(65) Prior Publication Data

US 2008/0152725 A1 Jun. 26, 2008
US 2012/0015046 A9 Jan. 19, 2012

Related U.S. Application Data

(63) Continuation-in-part of application No. 10/790,027, filed on Mar. 2, 2004, now Pat. No. 7,390,509, which is a continuation of application No. 10/315,159, filed on Dec. 10, 2002, now Pat. No. 6,814,983.

(51) Int. Cl.
*A01N 59/20* (2006.01)

(52) U.S. Cl.
USPC .......................................... 424/638

(58) Field of Classification Search
USPC .......................................... 424/638
See application file for complete search history.

(56) References Cited

U.S. PATENT DOCUMENTS

| | | |
|---|---|---|
| 1,869,721 A * | 8/1932 | Sure .................. 424/750 |
| 3,160,564 A | 12/1964 | Hanus |
| 3,608,083 A | 9/1971 | Bunnell |
| 3,846,550 A | 11/1974 | Akrongold |
| 4,124,710 A | 11/1978 | Descamps |
| 4,251,550 A | 2/1981 | Proctor |
| 4,374,082 A | 2/1983 | Hochschild |
| 4,431,634 A | 2/1984 | Ellenbogen |
| 4,547,488 A | 10/1985 | Merkel |
| 4,619,829 A | 10/1986 | Motschan |
| 4,710,387 A | 12/1987 | Uiterwaal et al. |
| 4,740,373 A | 4/1988 | Kesselman et al. |
| 4,752,479 A | 6/1988 | Briggs et al. |
| 4,804,535 A | 2/1989 | Kesselman et al. |
| 4,814,102 A | 3/1989 | Baur et al. |
| 4,863,898 A | 9/1989 | Ashmead et al. |
| 4,940,658 A | 7/1990 | Allen et al. |
| 4,945,083 A | 7/1990 | Jansen |
| 4,994,283 A | 2/1991 | Mehansho et al. |
| 5,108,767 A | 4/1992 | Mulchandani et al. |
| 5,215,750 A | 6/1993 | Keane |
| 5,215,754 A | 6/1993 | Valorose et al. |
| 5,278,329 A | 1/1994 | Anderson |
| 5,340,315 A | 8/1994 | Kaye |
| 5,340,594 A | 8/1994 | Barclay |
| 5,374,560 A | 12/1994 | Allen et al. |
| 5,407,957 A | 4/1995 | Kyle et al. |
| 5,438,017 A | 8/1995 | Allen |
| 5,457,055 A | 10/1995 | Allen et al. |
| 5,492,938 A | 2/1996 | Kyle et al. |
| 5,494,678 A | 2/1996 | Paradissis et al. |
| 5,514,382 A | 5/1996 | Sultenfuss |
| 5,556,644 A | 9/1996 | Chandra |
| 5,563,126 A | 10/1996 | Allen et al. |
| 5,569,458 A | 10/1996 | Greenberg |
| 5,626,884 A | 5/1997 | Lockett |
| 5,686,429 A | 11/1997 | Lin et al. |
| 5,770,215 A | 6/1998 | Moshyedi |
| 5,780,451 A | 7/1998 | DeMichele et al. |
| 5,795,873 A | 8/1998 | Allen |
| 5,869,084 A | 2/1999 | Paradissis et al. |
| 5,898,036 A | 4/1999 | McLeod |
| 5,914,129 A | 6/1999 | Mauskop |

(Continued)

FOREIGN PATENT DOCUMENTS

| | | | |
|---|---|---|---|
| EP | 0266323 | * | 6/1988 |
| EP | 0482715 | | 4/1992 |

(Continued)

OTHER PUBLICATIONS

Sunita R. Cheruku et al., "Higher maternal plasma docosahexaenoic acid during pregnancy is associated with more mature neonatal sleep-state patterning", AM J Clin Nutr 76:608-613 (2002).

Sharlene M. Day et al., "Chronic iron administration increases vascular oxidative stress and accelerates arterial thrombosis", Circulation 2003, 107: 2601-2606 (2003).

Michele DiStefano et al., Gastroenterol "Lactose malabsorption and intolerance and peak bone mass", vol. 122(7):1793-1799 (2002).

F. Facchinetti et al., "European review for medical and pharmacological sciences", vol. 9(1):41-48 (2005).

(Continued)

*Primary Examiner* — Jeffrey S. Lundgren
*Assistant Examiner* — Ibrahim D Bori
(74) *Attorney, Agent, or Firm* — Don J. Pelto, Esquire; Sheppard, Mullin, Richter & Hampton LLP

(57) ABSTRACT

The present invention relates to methods of co-administration of various vitamin and mineral compositions, and in a specific embodiment, said methods comprise co-administering one composition comprising vitamin A, vitamin D, vitamin C, vitamin E, folic acid, vitamin $B_1$, vitamin $B_2$, vitamin $B_6$, vitamin $B_{12}$, niacin, calcium, iron, magnesium, zinc, and/or copper, and a second composition comprising omega-3 fatty acids such as DHA, to supplement the nutritional needs of individuals within physiologically stressful states; and kits provided for co-administration of various vitamin and mineral compositions, and in a specific embodiment, said kits comprise one composition comprising vitamin A, vitamin D, vitamin C, vitamin E, folic acid, vitamin $B_1$, vitamin $B_2$, vitamin $B_6$, vitamin $B_{12}$, niacin, calcium, iron, magnesium, zinc, and/or copper, and a second composition comprising omega-3 fatty acids such as DHA, to supplement the nutritional needs of individuals within physiologically stressful states.

26 Claims, No Drawings

(56) References Cited

U.S. PATENT DOCUMENTS

| | | |
|---|---|---|
| 5,922,704 A | 7/1999 | Bland |
| RE36,288 E | 8/1999 | Lin et al. |
| 5,932,624 A | 8/1999 | Herbert |
| 5,948,443 A | 9/1999 | Riley |
| 5,965,162 A | 10/1999 | Fuisz et al. |
| 5,976,568 A | 11/1999 | Riley |
| 5,997,915 A | 12/1999 | Bailey |
| 6,039,978 A | 3/2000 | Bangs et al. |
| 6,042,849 A | 3/2000 | Richardson |
| 6,048,846 A | 4/2000 | Cochran |
| 6,054,128 A | 4/2000 | Wakat |
| 6,090,414 A | 7/2000 | Passwater |
| 6,093,425 A | 7/2000 | Kamarei |
| 6,102,706 A | 8/2000 | Khoo et al. |
| 6,103,756 A | 8/2000 | Gorsek |
| 6,136,345 A | 10/2000 | Grimmett |
| 6,136,859 A | 10/2000 | Henriksen |
| 6,139,872 A | 10/2000 | Walsh |
| 6,207,651 B1 | 3/2001 | Allen |
| 6,214,373 B1 | 4/2001 | Snowden |
| 6,218,192 B1 | 4/2001 | Altura et al. |
| 6,228,388 B1 | 5/2001 | Paradissis et al. |
| 6,245,360 B1 | 6/2001 | Markowitz |
| 6,255,341 B1 | 7/2001 | DeMichele et al. |
| 6,258,846 B1 * | 7/2001 | Hermelin et al. ............ 514/558 |
| 6,297,224 B1 | 10/2001 | Allen et al. |
| 6,299,896 B1 | 10/2001 | Cooper et al. |
| 6,352,713 B1 | 3/2002 | Kirschner et al. |
| 6,361,800 B1 | 3/2002 | Cooper et al. |
| 6,410,281 B1 | 6/2002 | Barclay |
| 6,440,450 B1 | 8/2002 | Han |
| 6,444,218 B2 | 9/2002 | Han |
| 6,447,809 B1 | 9/2002 | Krumhar et al. |
| 6,451,341 B1 | 9/2002 | Slaga et al. |
| 6,451,567 B1 | 9/2002 | Barclay |
| 6,488,956 B1 | 12/2002 | Paradissis et al. |
| 6,495,177 B1 | 12/2002 | deVries et al. |
| 6,500,472 B2 | 12/2002 | Uchida et al. |
| 6,521,247 B1 | 2/2003 | deVries |
| 6,528,496 B1 | 3/2003 | Allen et al. |
| 6,569,445 B2 | 5/2003 | Manning et al. |
| 6,572,888 B2 | 6/2003 | Byrd |
| 6,576,253 B2 | 6/2003 | Manning et al. |
| 6,579,544 B1 | 6/2003 | Rosenberg |
| 6,607,900 B2 | 8/2003 | Bailey et al. |
| 6,660,293 B2 | 12/2003 | Giordano et al. |
| 6,814,983 B2 | 11/2004 | Giordano et al. |
| 6,818,228 B1 | 11/2004 | Walsdorf et al. |
| 6,849,613 B2 | 2/2005 | Prasad |
| 6,866,873 B2 | 3/2005 | Stern |
| 6,914,073 B2 | 7/2005 | Boulos et al. |
| 6,977,167 B2 | 12/2005 | Barclay |
| 7,390,509 B2 | 6/2008 | Giordano et al. |
| 7,422,758 B2 | 9/2008 | Block et al. |
| 7,704,542 B2 | 4/2010 | Bydlon et al. |
| 2001/0028897 A1 | 10/2001 | Hammerly |
| 2002/0015742 A1 | 2/2002 | Jackson et al. |
| 2002/0025310 A1 | 2/2002 | Bland |
| 2002/0034543 A1 | 3/2002 | Kirschner et al. |
| 2002/0044969 A1 | 4/2002 | Harden et al. |
| 2002/0102330 A1 * | 8/2002 | Schramm et al. ............ 426/72 |
| 2002/0169209 A1 * | 11/2002 | Horrobin ............... 514/560 |
| 2002/0187205 A1 | 12/2002 | Paradissis et al. |
| 2002/0192265 A1 | 12/2002 | Manning et al. |
| 2003/0049352 A1 | 3/2003 | Mehansho et al. |
| 2003/0060509 A1 | 3/2003 | Elswyk |
| 2003/0068372 A1 | 4/2003 | Kirschner et al. |
| 2003/0108594 A1 | 6/2003 | Manning et al. |
| 2003/0206969 A1 | 11/2003 | Nidamarty et al. |
| 2004/0043043 A1 | 3/2004 | Schlyter et al. |
| 2005/0170479 A1 | 8/2005 | Weaver |
| 2006/0034912 A1 | 2/2006 | Giordano et al. |
| 2006/0034916 A1 | 2/2006 | Giordano et al. |
| 2006/0088574 A1 | 4/2006 | Manning et al. |
| 2006/0099693 A1 | 5/2006 | Kobzeff et al. |
| 2006/0153824 A1 * | 7/2006 | Giordano et al. ............ 424/94.1 |
| 2006/0165735 A1 | 7/2006 | Abril et al. |
| 2006/0217385 A1 * | 9/2006 | Edwards et al. ............ 514/251 |
| 2008/0274175 A1 * | 11/2008 | Schramm et al. ............ 424/456 |

FOREIGN PATENT DOCUMENTS

| | | |
|---|---|---|
| EP | 0891719 | 1/1999 |
| GB | 822127 | 10/1959 |
| GB | 975387 | 11/1964 |
| JP | 2003012554 | 1/2003 |
| JP | 2003159028 | 6/2003 |
| WO | 99/07419 | 2/1999 |

OTHER PUBLICATIONS

Cindy A. Francois et al., "Supplementing lactating women with flaxseed oil does not increase docosahexaenoic acid in their milk", AM J Clin Nutr., 77:226-33 (2003).

Ingrid B. Helland et al.. Pediatrics "Maternal supplementation with very-long-chain n-3 fatty acids during pregnancy and lactation augments children's IQ at 4 years of age", 111:39-44 (2003).

Monique DM Al et al., "Long-chain polyunsaturated fatty acids, pregnancy, and pregnancy outcome", AM J Clin Nutr 71:285S-291S (2000).

Frank B. Hu et al., JAMA, vol. 287 (14); 1815-1821 (2002).

M.K. Javaid et al., "Material vitamin D status during pregnancy and childhood bone mass at age 9 years: a longitudinal study", The Lancet vol. 367(9504):36-43 (2006).

M. Hørby Jørgensen et al., "Visual acuity and erythrocyte docosahexaenoic acid status in breast-fed and formula-fed term infants during the first four months of life" Lipids, vol. 31(1):99-105 (1996).

Daniel Kurnik et al., "Multivitamin supplements may affect warfarin anticoagulation in susceptible patients", Annals of pharmacotherapy, vol. 37(11):1603-06 (2003).

Maggie Laidlaw and Bruce J. Holub, "Effects of supplementation with fish oil-derived n-3 fatty acids and •-linolenic acid on circulating plasma lipids and fatty acid profiles in women" AM J Clin Nutr 77:37-42 (2003).

Robert K. McNamara et al., "Modulation of phosphoinositide-protein kinase C signal transduction by omega-3 fatty acids: Implications for the pathophysiology and treatment of recurrent neuropsychiatric illness", vol. 75(4-5):237-57 (2006).

Martha Neuringer et al., "n-3 Fatty acids in the brain and retina: Evidence for their essentiality", vol. 44:285-294 (1986).

S. J. Otto et al., "Increased risk of postpartum depressive symptoms is associated with slower normalization after pregnancy of the functional docosahexaenoic acid status", vol. 69 (3):237-243 (2003).

Gordon Parker et al., "Omega-3 Fatty acids and mood disorders", AM J Psychiatry 163(6):969-978 (2006).

France M. Rioux et al., "Does inadequate maternal iron or DHA status have a negative impact on an infant's functional outcomes?", Acta Paediatrica, vol. 95(2):137-144 (2006).

M J Shearer, "Vitamin K", The Lancet; vol. 345:229-34 (1995).

Cornelius M. Smuts et al., "A Randomized trial of docosahexaenoic acid supplementation during the third trimester of pregnancy"; The American College of Obstetricians and Gynecologists, vol. 101(3):469-479 (2003).

Laura J. Stevens et al., "Omega-3 Fatty acids in boys with behavior learning, and health problems", Physiology & Behavior, vol. 59:915-920 (1996).

Basil A. Stoll, "n-3 Fatty acids and lipid peroxidation in breast cancer inhibition", Journal of Nutrition, vol. 87(3):193-198 (2002).

John B. Vincent, "The potential value and toxicity of chromium picolinate as a nutritional supplement, weight loss agent and muscle development agent", Sports Medicine, vol. 33(3):213-30 (2003).

Clemens Von Schacky et al., "The effect of dietary •-3 Fatty acids on coronary atherosclerosis a Randomized, double-blind, placebo-Controlled trial", vol. 130:554-562 (1999).

Genevieve S. Young et al., "Effect of randomized supplementation with high does olive, flax or fish oil on serum phospholipid fatty acid levels in adults with attention deficit hyperactivity disorder", Reprod. Nutr. Dev. vol. 45 :549-558 (2005).

(56) References Cited

OTHER PUBLICATIONS

Martel( Product Specifications Dhasco®-T, Vegetable oil from microalgae, containing 40% docosahexaenoic acid (DHA).
Vitafol®-OB, "Vitamin & mineral caplets for use before, during and after pregnancy", V1-5/05.
Seager, 50 J. Pharm. Pharmacol. 375-82 (1998).
Lapido, 72 (Supp.) Amer. J. Clin. Nutr. 280S-90S (2000).
Black, 85(2)(Supp.) Brit. J. Nutr. S193-S97 (2001).
Scholl et al., (146)(2) Amer. J. Epidem. 134-41 (1997).
Zile et al., 131(3) J. Nutr. 705-08 (2001).
Mayne, 10 J. FASEB 690-701 (1996).
Rock et al., 96(7) J. Amer. Diet. Assoc. 693-702 (1996).
Myatt & Cui, 122(4) Histochem. Cell. Biol. 369-82 (2004).
Llurba et al., 37(4) Free Radic. Biol. Med. 557-70 (2004).
Lee et al., 58(3) Eur. J. Clin. Nutr. 481-7 (2004).
Henkin et al., 91(3) AM. J. Med. 239-46 (1991).
Bostom et al., 49(1) Kidney Int. 147-52 (1996).
Robinson et al., 94 Circulation 2743-48 (1996).
Locksmith & Duff, 91(6) Obstet. Gynecol. 1027-34 (1998).
Van Der Put et al., Exp. Biol. Med. 116(4) 243-70 (2001).
Defalco et al., 27 Clin. Exp. Obstet. Gynecol. 188-90 (2000).
Eskes, 27 Clin Exp. Obstet. Gynecol. 157-67 (2000).
Woods et al., 185(1)AM. J. Obstet. Gynecol. 5-10 (2001).
Kharb, 93(1) Euro. J. Obstet. Gynecol. Reprod. Biol. 37-39 (2000).
Milczarek et al., 210 Mol. Cell. Biochem. 65-73 (2000).
Dawson-Hughes et al., 337 New Eng. J. Med. 670-76 (1997).
Lips et al., 86 J. Clin. Endocrinol. Metab. 1212-21 (2001).
Stampfer et al., 328 New Eng. J. Med. 1444-49 (1993).
Bothwell, 72(Supp.) AM. J. Clin. Nutr. 257S-64S (2000).
Sifakis & Pharmakides, 900 Ann. N.Y. Acad. Sci. 125-36 (2000).
Groff et al., Advanced Nutrition and Human Metabolism 341 (2d ed. 1996).
Agus et al., 17 Crit. Care Clin. 175-87 (2001).
Shechter et al., 102 Circulation 2353-58 (2000).
Zima et al., 17(4) Blood Purif. 182-86 (1999).
Srinivas et al., 68(6) Indian J. Pediatr. 519-22 (2001).
Yang et al., 13(4) Biomed. Environ. Sci. 280-86 (2000).
King, 71 (Supp.) AM. J. Clin. Nutr. 1334S-43S (2000).
Horrocks et al., Health Benefits of Docosahexaenoic Acid (DHA): Pharmacological Research, 1999, Vo. 40, No. 3, pp. 211-225, Abstract p. 212, col. 2, para 2.
Everett Laboratories, Inc.'s Complaint against River's Edge Pharmaceuticals, LLC, filed Jul. 14, 2009.
Everett Laboratories, Inc.'s Notice of Motion for Preliminary Injunction as to Trademark Claims, filed Jul. 31, 2009.
Everett Laboratories, Inc.'s Notice of Motion for Preliminary Injunction as to Patent Claims, filed Jul. 31, 2009.
Defendant's Brief in Opposition to Plaintiff's Motion for Preliminary Injunction, filed Aug. 25, 2009.
Plaintiff's Reply Brief in Support to Plaintiff's Motion for Preliminary Injunction as to Patent Claims, filed Sep. 2, 2009.
Plaintiff's Reply Brief in Support to Plaintiff's Motion for Preliminary Injunction as to Trademark Claims, filed Sep. 2, 2009.
Physicians Desk Reference, 1999 Edition, Vitafol-PN Caplet Product.
Amine et al., J, Nutrition, 101: 927-936 (1971).
Select—OB™ Product Insert, Jul. 2005.
Order granting motion to stay litigation pending reexamination, Nov. 24, 2009.
1st Reexamination Request, Jul. 14, 2009.
Notice of Failure to Comply with Ex Parte Reexamination Request Filing Requirements, Jul. 27, 2009.
Reply to Notice of Failure to Comply with Ex Parte Reexamination Request Fling Requirements, Aug. 13, 2009.
2nd Reexamination Request, Sep. 18, 2009.
Order Granting Reexamination, Oct. 23, 2009.
PDR for Nutritional Supplements, selected pages, 2001.
Pediatric Dental Health, May 22, 2004.
Perspectives in Nutrition, selected pages, 5th Edition, 2002.
Allman et al., 150 Med. J. Australia 130-33 (1999).
Anderson et al., 54 Am. J. Clin. Nutr. 909-916 (1991).
Anderson, 26 Diabetes & Metabolism (Paris) 22-27 (2000).
Bazzarre et al., 12(2) J. Amer. Coll. Nutr. 162-69 (1993).
Berendschot et al., 41 Invest. Ophthalmol. Vis. Sci. 3322-3326 (2000).
Bernstein et al., 72 Exp. Eye Res. 215-223 (2001).
Blumberg et al., 20(5) Clin. Nephrol. 244-50 (1983).
Braguer et al., 57 Nephron 192-96 (1991).
Burk, 3 Biological Activity of Selenium 53-70 (1983).
Burton et al., Ann. NY Acad. Sci. 7-22 (1998).
Carr et al. 87 Circ. Res. 349-354 (2000).
Cattaneo, 32(Supp 1) Ann. Med. 46-52 (2000).
Shankar et al., 68 Amer. J. Clin. Nutr. 447S-463S (1998).
Christian et al., 130(11) J. Nutr. 2675-82 (2000).
Stein et al., 3 Blood Purification 52-62 (1985).
Descombes et al., 24(10) Artificial Organs 773-78 (2000).
Dierkes et al., 11(2) J. Renal Nutr. 67-72 (2001).
Story et al., 27(1) Crit. Care Med. 220-23 (1999).
Shah et al., 18(1) Amer. J. Kidney Dis. 84-90 (1991).
Frank et al., 70(4) Int. J. Vitam. Nutr. Res. 159-66 (2000).
Haberland et al., 113(2) Amer. Heart J. 573-577 (1987).
Hanratty et al., 85 Heart 326-330 (2001).
Uauy et al., 67 Amer. J. Clin. Nutr. 952S-959S (1998).
Heller et al., 276 J. Biol. Chem. 40-47 (2001).
Henkin et al., 91 Amer. J. Med. 239-246 (1991).
Henning et al., 95(9) Medizin. Klinik 477-81 (2000).
Henriksen et al., 3(2) Arteriosclerosis 149-159 (1983).
Holben et al., 99(7) Journal of the American Dietetic Assoc. 836-843 (1999).
Hoogeveen et al., 101 Circulation 1506-1511 (2000).
House et al., 45(1) ASAIO J. 94-97 (1999).
Huang et al., 275(23) J. Biol. Chem. 17399-17406 (2000).
Islam et al., 150 Astherosclerosis 217-224 (2000).
Jaarsveld et al., 99(1) Res. Comm. Mol. Pathol. Pharmacol. 69-80 (1988).
Kagan et al., 44(8) Biochem. Pharmacol. 1637-1649 (1992).
Kang-Yoon et al., 56 Am. J. Clin. Nutr. 548-58 (1992).
Kim, 57(10) Nutr. Reviews 314-21 (1999).
Kishi et al., 48 Diabetes 2045-2051 (1999).
Lemke et al., 44 J. Lipid Res. 1591-1600 (2003).
Locksmith et al., 91(6) Obstet. Gynecol. 1027-34 (1998).
Makoff, 25 Miner. Electrolyte Metab. 349-51 (1999).
Mares-Periman et al., 153(5) Amer. J. Epidemiol. 424-432 (2001).
Morris et al., 13 J. Trace Elements Med. Biol. 57-61 (1999).
Moser-Veillon et al., 52 Am. J. Clin. Nutr. 135-41 (1990).
Vincent, 33(3) Sports Medicine 213-30 (2003).
Naude et al., 40(12) Journal of Clinical Pharmacology. 1447-51, (abstract only) (2000).
Vos, 161 Arch. Intern. Med. 774-75 (2001).
Weigel et al., 12 Cont. Clin. Trials 378-94 (1991).
Omenn et al., 334(18) New Eng. J. Med. 1150-1155 (1996).
O'Neil-Cutting et al., The effect of antacids on the absorption of simultaneously ingested iron, JAMA 255,1468-1470 (1986).
Zacharski et al., 139(2) Amer. Heart J. 337-345 (2000).
Parfrey, 23 Advances in Nephrology 311-330 (1994).
Perna et al., 25 Mineral and Electrolyte Metabolism 95-99 (1999).
Purkkala-Sarataho et al., 20 Arteriescler. Thromb. Vasc. Biol. 2087-2093 (2000).
Rapp et al., 41 Invest. Ophthalmol. Vis. Sci. 1200-1209 (2000).
Rudich et al., 42 Dabetologia 949-957 (1999).
Schlaich et al., 153 Atherosclerosis 383-389 (2000).
Easterbauer et al., Free Rad. Biol. Med. 341-390 (1992).
The VITATOPS Trial Study Group, 13 Cerebrovasc. Dis. 120-26 (2002).
Viitafol® product insert, Jul. 1997.
Vitafol® Syrup product label, 1997.
Vitafol®-PN product insert, Apr. 1997.
Shah et al., 20(1) Am. J. Kidney Diseases 42-49 (1992).
Vitafol®-OB product insert, Nov. 2004.
*Complaint, Everett Laboratories, Inc.*, v. *Acella Pharmaceuticals, LLC*, Case No. 2:33-av-00001 (U.S. Dist. Ct. Dist. of NJ. Filed Jun. 6, 2013).

(56) References Cited

OTHER PUBLICATIONS

Plaintiffs Proposed Order Granting Motion for Preliminary Injunction, *Everett Laboratories, Inc., v. Acella Pharmaceuticals, LLC*, Case No. 2:13-cv-03529-ES-SCM (U.S. Dist. Ct. Dist. of NJ. Filed Jul. 2, 2013).
Brief in Support of Plaintiffs Motion for Preliminary Injunction, *Everett Laboratories, Inc., v. Acella Pharmaceuticals, LLC*, Case No. 2:13-cv-03529-ES-SCM (U.S. Dist. Ct. Dist. of NJ. Filed Jul. 2, 2013).
Declaration of Bruce Brown in Support of Motion for Preliminary Injunction, *Everett Laboratories, Inc., v. Acella Pharmaceuticals, LLC*, Case No. 2:13-cv-03529-ES-SCM (U.S. Dist. Ct. Dist. of NJ. Filed Jul. 2, 2013).
Declaration of Alisha Nielsen in Support of Motion for Preliminary Injunction, *Everett Laboratories, Inc., v. Acella Pharmaceuticals, LLC*, Case No. 2:13-cv-03529-ES-SCM (U.S. Dist. Ct. Dist. of NJ. Filed Jul. 2, 2013).
Declaration of Jitka Shavel in Support of Motion for Preliminary Injunction, *Everett Laboratories, Inc., v. Acella Pharmaceuticals, LLC*, Case No. 2:13-cv-03529-ES-SCM (U.S. Dist. Ct. Dist. of NJ. Filed Jul. 2, 2013).
Declaration of Lucas Sigman in Support of Motion for Preliminary Injunction, *Everett Laboratories, Inc., v. Acella Pharmaceuticals, LLC*, Case No. 2:13-cv-03529-ES-SCM (U.S. Dist. Ct. Dist. of NJ. Filed Jul. 2, 2013).
Declaration of Robert J. Schoenberg in Support of Motion for Preliminary Injunction, *Everett Laboratories, Inc., v. Acella Pharmaceuticals, LLC*, Case No. 2:13-cv-03529-ES-SCM (U.S. Dist. Ct. Dist. of NJ. Filed Jul. 2, 2013).
Exhibits 1-3, to Robert J. Schoenberg Declaration, *Everett Laboratories, Inc., v. Acella Pharmaceuticals, LLC*, Case No. 2:13-cv-03529-ES-SCM (U.S. Dist. Ct. Dist. of NJ. Filed Jul. 2, 2013).
Exhibits 4-5, to Robert J. Schoenberg Declaration, *Everett Laboratories, Inc., v. Acella Pharmaceuticals, LLC*, Case No. 2:13-cv-03529-ES-SCM (U.S. Dist. Ct. Dist. of NJ. Filed Jul. 2, 2013).
Exhibits 6-7, to Robert J. Schoenberg Declaration, *Everett Laboratories, Inc., v. Acella Pharmaceuticals, LLC*, Case No. 2:13-cv-03529-ES-SCM (U.S. Dist. Ct. Dist. of NJ. Filed Jul. 2, 2013).
Exhibits 8-10, to Robert J. Schoenberg Declaration, *Everett Laboratories, Inc., v. Acella Pharmaceuticals, LLC*, Case No. 2:13-cv-03529-ES-SCM (U.S. Dist. Ct. Dist. of NJ. Filed Jul. 2, 2013).
Exhibits 11-14, to Robert J. Schoenberg Declaration, *Everett Laboratories, Inc., v. Acella Pharmaceuticals, LLC*, Case No. 2:13-cv-03529-ES-SCM (U.S. Dist. Ct. Dist. of NJ. Filed Jul. 2, 2013).
Exhibits 15-18, to Robert J. Schoenberg Declaration, *Everett Laboratories, Inc., v. Acella Pharmaceuticals, LLC*, Case No. 2:13-cv-03529-ES-SCM (U.S. Dist. Ct. Dist. of NJ. Filed Jul. 2, 2013).
Exhibits 19-30, to Robert J. Schoenberg Declaration, *Everett Laboratories, Inc., v. Acella Pharmaceuticals, LLC*, Case No. 2:13-cv-03529-ES-SCM (U.S. Dist. Ct. Dist. of NJ. Filed Jul. 2, 2013).
Answer and Counterclaim of Defendent Acella Pharmaceuticals, LLC, *Everett Laboratories, Inc., v. Acella Pharmaceuticals, LLC*, Case No. 1:13-cv-03529-JEI-KMW (U.S. Dist. Ct. Dist. of NJ. Filed Jul. 24, 2013).
Declaration of Mary M. Bridgeman, *Everett Laboratories, Inc., v. Acella Pharmaceuticals, LLC*, Case No. 1:13- cv-03529-JEI-KMW (U.S. Dist. Ct. Dist. of NJ. Filed Aug. 8, 2013).
Exhibits A-F, to Mary M. Bridgeman Declaration, *Everett Laboratories, Inc., v. Acella Pharmaceuticals, LLC*, Case No. 1:13-cv-03529-JEI-KMW (U.S. Dist. Ct. Dist. of NJ. Filed Aug. 8, 2013).
Exhibits G-O, to Mary M. Bridgeman Declaration, *Everett Laboratories, Inc., v. Acella Pharmaceuticals, LLC*, Case No. 1:13-cv-03529-Jei-Kmw (U.S. Dist. Ct. Dist. of NJ. Filed Aug. 8, 2013).
Exhibits P-S, to Mary M. Bridgeman Declaration, *Everett Laboratories, Inc., v. Acella Pharmaceuticals, LLC*, Case No. 1:13-cv-03529-JEI-KMW (U.S. Dist. Ct. Dist. of NJ. Filed Aug. 8, 2013).
Declaration of Harry G. Brittain, *Everett Laboratories, Inc., v. Acella Pharmaceuticals, LLC*, Case No. 1:13-cv-03529- JEI-KMW (U.S. Dist. Ct. Dist. of NJ. Filed Aug. 8, 2013).
Exhibits A-F, to Harry G. Brittain Declaration, *Everett Laboratories, Inc., v. Acella Pharmaceuticals, LLC*, Case No. 1:13-cv-03529-JEI-KMW (U.S. Dist. Ct. Dist. of NJ. Filed Aug. 8, 2013).
Exhibits G-S, to Harry G. Brittain Declaration, *Everett Laboratories, Inc., v. Acella Pharmaceuticals, LLC*, Case No. 1:13-cv-03529-JEI-KMW (U.S. Dist. Ct. Dist. of NJ. Filed Aug. 8, 2013).
Declaration of Bryce R. Cook, *Everett Laboratories, Inc., v. Acella Pharmaceuticals, LLC*, Case No. 1:13-cv-03529-JEI-KMW (U.S. Dist. Ct. Dist. of NJ. Filed Aug. 8, 2013).
Exhibits A-B, to Bryce R. Cook Declaration, *Everett Laboratories, Inc., v. Acella Pharmaceuticals, LLC*, Case No. 1:13-cv-03529-JEI-KMW (U.S. Dist. Ct. Dist. of NJ. Filed Aug. 8, 2013).
Declaration of Harold Arthur Deas, *Everett Laboratories, Inc., v. Acella Pharmaceuticals, LLC*, Case No. 1:13-cv-03529-JEI-KMW (U.S. Dist. Ct. Dist. of NJ. Filed Aug. 8, 2013).
Exhibits A-C, to Harold Arthur Deas Declaration, *Everett Laboratories, Inc., v. Acella Pharmaceuticals, LLC*, Case No. 1:13-cv-03529-JEI-KMW (U.S. Dist. Ct. Dist. of NJ. Filed Aug. 8, 2013).
Declaration of Roger Beemer Newman, M.D., *Everett Laboratories, Inc., v. Acella Pharmaceuticals, LLC*, Case No. 1:13-cv-03529-JEI-KMW (U.S. Dist. Ct. Dist. of NJ. Filed Aug. 8, 2013).
Exhibits A-E, to Roger Beemer Newman, M.D., Declaration, *Everett Laboratories, Inc., v. Acella Pharmaceuticals, LLC*, Case No. 1:13-cv-03529-JEI-KMW (U.S. Dist. Ct. Dist. of NJ. Filed Aug. 8, 2013).
Defendant Acella Pharmaceuticals, LLC's Memorandum in Opposition to Plaintiffs Motion for a Preliminary Injunction, *Everett Laboratories, Inc., v. Acella Pharmaceuticals, LLC*, Case No. 1:13-cv-03529-JEI-KMW (U.S. Dist. Ct. Dist. of NJ. Filed Aug. 8, 2013).
Defendant Acella Pharmaceuticals, LLC's Amended Memorandum in Opposition to Plaintiffs Motion for a Preliminary Injunction, *Everett Laboratories, Inc., v. Acella Pharmaceuticals, LLC*, Case No. 1:13-cv-03529-JEI-KMW (U.S. Dist. Ct. Dist. of NJ. Filed Aug. 10, 2013).
Reply in Support of Plaintiffs Motion for Preliminary Injunction, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Reply Declaration of Lucas Sigman, in Support of Motion to Preliminary Injunction, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Exhibit A, to Lucas Sigman Reply Declaration, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Exhibit B, to Lucas Sigman Reply Declaration, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Exhibit C, to Lucas Sigman Reply Declaration, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Exhibit D, to Lucas Sigman Reply Declaration, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Reply Declaration of Robert J. Schoenberg, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Exhibit 1, to Robert J. Schoenberg Reply Declaration, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Exhibits 2, to Robert J. Schoenberg Reply Declaration, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Exhibits 3-4, to Robert J. Schoenberg Reply Declaration, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Reply Declaration of Alisha Nielsen, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).

(56) References Cited

OTHER PUBLICATIONS

Reply Declaration of Bruce Brown, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Reply Declaration of Brian C. Reisetter, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Reply Declaration of Douglas Gary Lichtman, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Reply Declaration of Walter Bratic, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Declaration of Lynn B. Bailey, Ph.D., *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Reply Declaration of Lee P. Shulman, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Exhibits A-B, to Lee P. Shulman Reply Declaration, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Exhibit C, to Lee P. Shulman Reply Declaration, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Exhibit D, to Lee P. Shulman Reply Declaration, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Declaration of Yashoda V. Pramar, Ph.D., *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Supplemental Reply Declaration Part 1 of Jitka Shavel, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Supplemental Reply Declaration Part 2 of Jitka Shavel, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Declaration of Joseph Schramm, III, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).
Exhibit A-C, to Joseph Schramm, III, Declaration, *Everett Laboratories, Inc., v. Acella Pharmaceuticals, LLC*, Case No. 1:13-cv-03529-JEI-KMW (U.S. Dist. Ct. Dist. of NJ. Filed Aug. 16, 2013).

\* cited by examiner

METHODS AND KITS FOR CO-ADMINISTRATION OF NUTRITIONAL SUPPLEMENTS

CROSS REFERENCE TO RELATED APPLICATIONS

The Present application is a Continuation-In-Part of U.S. patent application Ser. No. 10/790,027, filed Mar. 2, 2004, now U.S. Pat. No. 7,390,509, issued Jun. 24, 2008, which is a Continuation of U.S. patent application Ser. No. 10/315,159, filed Dec. 10, 2002, now U.S. Pat. No. 6,814,983, issued Nov. 9, 2004.

FIELD OF THE INVENTION

The present invention relates to methods of co-administration of various vitamin and mineral compositions and kits provided for co-administration of these compositions for nutritional supplementation in, for example, subjects in physiologically stressful states.

BACKGROUND OF THE INVENTION

Nutrition plays a critical role in maintaining good health. Proper nutrition prevents dietary deficiencies, and also protects against the development of disease. Proper nutrition plays an increasingly important role as the body faces physiological stress. For example, pregnancy and lactation are among the most nutritionally volatile and physiologically stressful periods and processes in the lifetimes of women. Specifically, vitamin and mineral needs are almost universally increased during these natural processes. These increased needs are almost always due to elevated metabolic demand, increased plasma volume, increased levels of blood cells, decreased concentrations of nutrients, and decreased concentrations of nutrient-binding proteins.

Thus, nutritional supplementation serves a vital role in protecting against poor nutrition and disease. More specifically, research has suggested that optimizing specific nutrients before, during, and after the physiological processes of pregnancy or lactation can have a profound, positive, and comprehensive impact upon the overall wellness of the developing and newborn child as well as the safety and health of the mother. The present inventions provide compositions and methods designed to supplement the nutritional needs of individuals within physiologically stressful states.

Supplementation with certain vitamins and minerals serves a role in protecting against disease and contributes to the overall health of the mother and developing child. Specifically, such compounds as vitamin $B_6$, vitamin $B_{12}$, folic acid, and omega-3 fatty acids such as docosahexaenoic acid (DHA), play integral roles in physiological mechanisms that serve to prevent, treat and/or alleviate the occurrence or negative effects of some diseases. Supplementation with other vitamins and minerals, however, may inhibit the beneficial effects of these compounds. Thus, when choosing and administering a nutritional supplement, it is essential to understand the physiological needs and risks of individual patients and particular population groups, and the interactions between various vitamins and minerals.

SUMMARY OF THE INVENTION

The present invention provides methods of co-administering compositions and kits comprising compositions for both prophylactic and therapeutic nutritional supplementation. Specifically, for example, the present invention relates to novel compositions of vitamins and minerals that can be used to supplement the nutritional deficiencies observed in patients throughout physiologically stressful states. The present invention also may be formulated to exclude vitamins and minerals known to inhibit the beneficial effects of the included vitamins and minerals.

The present invention includes methods of co-administering the compositions of the invention to patients, together or in any order, to supplement the nutritional deficiencies observed in patients throughout physiologically stressful states such as, for example, pregnancy, lactation, and any disease state. The compositions of the present invention may be in a swallowable, chewable or dissolvable form according to an individual patient's preference. Choice in dosage form promotes ease of administration and compliance with dosing regimens.

The present invention also includes kits that may be provided to patients, wherein the compositions as described herein are packaged for co-administration to a patient.

In one embodiment of the present invention, the method comprises co-administering to a patient a first composition comprising vitamin A, vitamin D, vitamin C, vitamin E, folic acid, vitamin $B_1$, vitamin $B_2$, vitamin $B_6$, vitamin $B_{12}$, niacin, calcium, iron, magnesium, zinc, and copper; and, a second composition comprising omega-3 fatty acids.

In another embodiment, the method or kit comprises a second composition wherein the omega-3 fatty acid comprises docosahexaenoic acid (DHA).

In one embodiment, the method comprises co-administering the two compositions at the same time, or one after the other in either order.

In a specific embodiment, the compositions of the described method are co-administered to the patient orally. The compositions may be swallowable, chewable, or dissolvable.

In a specific embodiment, vitamin A comprises acetate, vitamin $B_1$ comprises thiamine mononitrate, and/or vitamin $B_6$ comprises pyridoxine hydrochloride. In another specific embodiment, folic acid comprises vitamin $B_9$, folacin, metafolin, or folate. In another embodiment, folic acid comprises one or more natural derivatives of folate, such as (6S)-tetrahydrofolic acid or a polyglutamyl derivative thereof, 5-methyl-(6S)-tetrahydrofolic acid or a polyglutamyl derivative thereof, 5-formyl-(6S)-tetrahydrofolic acid or a polyglutamyl derivative thereof, 10-formyl-(6R)-tetrahydrofolic acid or a polyglutamyl derivative thereof, 5,10-methylene-(6R)-tetrahydrofolic acid or a polyglutamyl derivative thereof, 5,10-methenyl-(6R)-tetrahydrofolic acid or a polyglutamyl derivative thereof, or 5-formimino-(6S)-tetrahydrofolic acid or a polyglutamyl derivative thereof.

In another embodiment, vitamin $B_{12}$ comprises cyanocobalamin, vitamin C comprises ascorbic acid, vitamin E comprises d-alpha tocopheryl acetate or d-alpha tocopheryl succinate, iron comprises ferrous fumarate, magnesium comprises magnesium oxide, and/or zinc comprises zinc oxide.

In a specific embodiment of the present invention, the first composition is substantially free of one or more of added compounds selected from the group consisting of vitamin A, vitamin D, vitamin C, vitamin E, folic acid, vitamin $B_1$, vitamin $B_2$, vitamin $B_6$, vitamin $B_{12}$, niacin, calcium, iron, magnesium, zinc, and copper.

In another embodiment of the present invention, the compositions are substantially free of other added active compounds. In a specific embodiment, the compositions of the present invention are substantially free of one or more of such added active compounds selected from the group consisting of lutein, lycopene, zeaxanthin, vitamin $B_4$, vitamin $B_5$, vitamin $B_7$, vitamin $B_8$, vitamin $B_{10}$, vitamin K, biotin, pantothenic acid, phosphorus, iodine, potassium, odorless garlic, coenzyme $Q_{10}$, 1-carnitine, grape seed extract, chloride, sodium, green tea extract, quercetin, fluoride, hawthorne berries, and alpha lipoic acid.

In another embodiment of the present invention, the compositions are substantially free added minerals. In a specific embodiment the compositions of the present invention are substantially free of one or more of added minerals selected from the group consisting of chromium, titanium, molybdenum, nickel, tin, silicon, vanadium, manganese, selenium, selenite, boron, bismuth, borax, bauxite, gold, silver, hydroxylapatite, mica, quartz, steatite, talc, sulfur, and zircon.

In another embodiment of the present invention, the compositions are substantially free of added inactive compounds that serve merely as inert, excipient, and/or formulatory ingredients of the composition. In a specific embodiment, the compositions of the present invention are substantially free of one or more of added inactive compounds selected from the group consisting of magnesium stearate, silica, silicon dioxide, magnesium silicate, dicalcium phosphate, povidone, titanium dioxide, sodium benzoate, alpha lipoic acid, lutein, lycopene, cellulose, croscarmellose sodium, stearic acid, cellulose, hydroxylpropyl cellulose, hydroxypropyl methylcellulose, titanium dioxide, polydextrose, triacetin, dicalcium phosphate, polyethylene glycol, polyvinylpyrrolidone, mineral oil, methocel, sodium lauryl sulfate, and talc.

In another embodiment, the method or kit includes a composition further comprising a pharmaceutically acceptable carrier. As an example but not by way of limitation, this carrier may be selected from one or more of the following: binders, diluents, lubricants, glidants, colorants, emulsifiers, disintegrants, starches, water, oils, alcohols, preservatives and sugars.

In another embodiment, the method or kit includes a composition that further comprises a sweetening agent. As an example but not by way of limitation, this sweetening agent may be one or more selected from the group consisting of sucrose, fructose, fructose, high fructose corn syrup, dextrose, saccharin sodium, maltodextrin, aspartame, potassium acesulfame, neohesperidin dihydrochalcone, sucralose, monoammonium glycyrrhizinate, and mixtures thereof.

In another embodiment, the method or kit includes a composition that further comprises a flavorant. As an example but not by way of limitation, the flavorant may be one or more selected from the group consisting of a natural flavor oil, a synthetic flavor oil, a citrus oil, a fruit essence, an extract from a plant, an extract from a leaf, an extract from a flower, an extract from a fruit, a synthetic flavor and a combination thereof. The flavorant may also be one or more selected from the group consisting of anise oil, cinnamon oil, peppermint oil, oil of wintergreen, clove oil, bay oil, anise oil, eucalyptus oil, thyme oil, cedar leave oil, oil of nutmeg, oil of sage, oil of bitter almonds, cassia oil, lemon oil, orange oil, lime oil, grapefruit oil, grape oil and a combination thereof. Or, the flavorant may be one or more selected from the group consisting of apple essence, pear essence, peach essence, berry essence, wildberry essence, date essence, blueberry essence, kiwi essence, strawberry essence, raspberry essence, cherry essence, plum essence, pineapple essence, and apricot essence. Additionally, the flavorant may be one or more selected from the group consisting of natural mixed berry flavor, citric acid, malic acid, vanilla, vanillin, cocoa, chocolate, and menthol.

In another specific embodiment, the method or kit includes a composition further comprising alkyl polysiloxane in an amount of about 0.05 weight percent to less than about 1.0 weight percent of either the first or the second composition. This alkyl polysiloxane may be in the form of dimethyl polysiloxane.

In one embodiment of the present invention, the method or kit is comprised of a composition comprising about 1350 IU to about 4050 IU of vitamin A; about 200 IU to about 600 IU of vitamin D; about 35 mg to about 105 mg of vitamin C; about 15 IU to about 45 IU of vitamin E; about 0.5 mg to about 1.5 mg of folic acid; about 0.8 mg to about 2.4 mg of vitamin B1; about 0.9 mg to about 2.7 mg of vitamin B2; about 1.25 mg to about 3.75 mg of vitamin B6; about 6 mcg to about 18 mcg of vitamin B12; about 9 mg to about 27 mg of niacin; about 50 mg to about 150 mg of calcium; about 32.5 mg to about 97.5 mg of iron; about 12.5 mg to about 37.5 mg of magnesium; about 12.5 mg to about 37.5 mg of zinc; and about 1 mg to about 3 mg of copper.

In another specific embodiment of the invention, the method or kit includes a composition comprising about 2700 IU vitamin A; about 400 IU vitamin D; about 70 mg vitamin C; about 30 IU vitamin E; about 1.0 mg folic acid; about 1.6 mg vitamin $B_1$; about 1.8 mg vitamin $B_2$; about 2.5 mg vitamin $B_6$; about 12 mcg vitamin $B_{12}$; about 18 mg niacin; about 100 mg calcium; about 65 mg iron; about 25 mg magnesium; about 25 mg zinc; and about 2 mg copper.

In a specific embodiment, the patient is pregnant, lactating, and/or has nutritional deficiencies. The nutritional deficiencies may be a result of pregnancy, lactation, elevated metabolic demand, or increased plasma volume, for example.

In another specific embodiment, the patient may be within a physiologically stressful state. This physiologically stressful state may be any disease state.

In another embodiment, the omega-3 fatty acids of the kit or method are enclosed in a gel-cap, or may be in liquid form.

In another specific embodiment, the omega-3 fatty acids of the kit or method are present in the amount of up to about 300 mg, about 75 mg to about 125 mg, about 90 mg to about 110 mg, or are present in the amount of about 100 mg.

In another embodiment, the kits are packaged in various forms including bottles and blister packs.

In yet another embodiment, the kits are packaged in bottles that are sold together; one bottle containing compositions comprising vitamin A, vitamin D, vitamin C, vitamin E, folic acid, vitamin $B_1$, vitamin $B_2$, vitamin $B_6$, vitamin $B_{12}$, niacin, calcium, iron, magnesium, zinc, and/or copper, and one bottle containing compositions comprising omega-3 fatty acids such as DHA.

In another embodiment, the kits are packaged in bottles that are sold separately; one bottle containing compositions comprising vitamin A, vitamin D, vitamin C, vitamin E, folic acid, vitamin $B_1$, vitamin $B_2$, vitamin $B_6$, vitamin $B_{12}$, niacin, calcium, iron, magnesium, zinc, and/or copper, and one bottle containing compositions comprising omega-3 fatty acids such as DHA.

In an alternative embodiment, the kits are packaged in bottles advertised as more effective if co-administered; one bottle containing compositions comprising vitamin A, vitamin D, vitamin C, vitamin E, folic acid, vitamin $B_1$, vitamin $B_2$, vitamin $B_6$, vitamin $B_{12}$, niacin, calcium, iron, magnesium, zinc, and/or copper, and one bottle containing compositions comprising omega-3 fatty acids such as DHA. The advertisements may consist of internet, print, and product packaging advertisements.

In another embodiment, the kits are packaged in blister packs that are sold together; one blister pack containing compositions comprising vitamin A, vitamin D, vitamin C, vitamin E, folic acid, vitamin $B_1$, vitamin $B_2$, vitamin $B_6$, vitamin $B_{12}$, niacin, calcium, iron, magnesium, zinc, and/or copper, and one blister pack containing compositions comprising omega-3 fatty acids such as DHA.

In yet another embodiment, the kits are packaged in one blister pack containing compositions comprising vitamin A, vitamin D, vitamin C, vitamin E, folic acid, vitamin $B_1$, vitamin $B_2$, vitamin $B_6$, vitamin $B_{12}$, niacin, calcium, iron, magnesium, zinc, and/or copper, and containing compositions comprising omega-3 fatty acids such as DHA, paired together per unit dose.

In another embodiment, the kits are packaged in blister packs that are sold separately; one blister pack containing compositions comprising vitamin A, vitamin D, vitamin C, vitamin E, folic acid, vitamin $B_1$, vitamin $B_2$, vitamin $B_6$, vitamin $B_{12}$, niacin, calcium, iron, magnesium, zinc, and/or copper, and one blister pack containing compositions comprising omega-3 fatty acids such as DHA.

In yet another embodiment, the kits are packaged in blister packs advertised as more effective if co-administered; one blister pack containing compositions comprising vitamin A, vitamin D, vitamin C, vitamin E, folic acid, vitamin $B_1$, vitamin $B_2$, vitamin $B_6$, vitamin $B_{12}$, niacin, calcium, iron, magnesium, zinc, and/or copper, and one blister pack containing compositions comprising omega-3 fatty acids such as DHA. The advertisements may consist of internet, print, and product packaging advertisements.

In another embodiment, the invention comprises a method which comprises providing the kit as described to patients.

Other objectives, features and advantages of the present invention will become apparent from the following detailed description. The detailed description and the specific examples, although indicating specific embodiments of the invention, are provided by way of illustration only. Accordingly, the present invention also includes those various changes and modifications within the spirit and scope of the invention that may become apparent to those skilled in the art from this detailed description.

DETAILED DESCRIPTION OF THE INVENTION

It is understood that the present invention is not limited to the particular methodologies, protocols, fillers, and excipients, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "a vitamin" is a reference to one or more vitamins and includes equivalents thereof known to those skilled in the art and so forth.

Unless defined otherwise, all technical and scientific terms used herein have the same meanings as commonly understood by one of ordinary skill in the art to which this invention belongs. Specific methods, devices, and materials are described, although any methods and materials similar or equivalent to those described herein can be used in the practice or testing of the present invention. All references cited herein are incorporated by reference herein in their entirety.

The term "disease state" as used herein, may comprise any state in which one or more organs or components of an organism malfunction. The term "disease state" may refer to any deterioration of any component of a body. The term "disease state" may refer to any deficiency of any compound necessary for the maintenance or function of any component of any organism. The term "disease state" may refer to any condition in which a body contains toxins, produced by microorganisms that infect the body or by body cells through faulty metabolism or absorbed from an external source. "Disease states" may be adverse states caused by any diet, any virus, or any bacteria. "Disease states" may comprise disorders associated with pregnant females such as, for example, osteomalacia and preeclampsia and disorders associated with a fetus such as, for example, neural tube defects and various fetal abnormalities. "Disease states" may comprise any pulmonary disorder such as, for example, bronchitis, bronchiectasis, atelectasis, pneumonia, diseases caused by inorganic dusts, diseases caused by organic dusts, any pulmonary fibrosis, and pleurisy. "Disease states" may comprise any hematological/oncological disorder such as, for example, anemia, hemophilia, leukemia, and lymphoma. A "disease state" may comprise any cancer such as, for example, breast cancer, lung cancer, prostate cancer, pancreatic cancer, liver cancer, stomach cancer, testicular cancer, ovarian cancer, skin cancer, cancer of the brain, cancer of the mouth, cancer of the throat, and cancer of the neck. "Disease states" may comprise any disorder of the immune system such as, for example, acquired immune deficiency syndrome (AIDS), AIDS-related complex, infection by any strain of any human immunodeficiency virus (HIV), and other viruses or pathogens such as bacteria, fungi and parasites. A "disease state" may comprise any cardiovascular disorder such as, for example, arterial hypertension, orthostatic hypotension, arteriosclerosis, coronary artery disease, cardiomyopathy, any arrhythmia, any valvular heart disease, endocarditis, pericardial disease, any cardiac tumor, any aneurysm, and any peripheral vascular disorder. "Disease states" may comprise any hepatic/biliary disorder such as, for example, jaundice, hepatic steatosis, fibrosis, cirrhosis, hepatitis, any hepatic granuloma, any liver tumor, cholelithiasis, cholecystitis, and choledocholithiasis.

The term "physiologically stressful state," as used herein, comprises any state of an organism in which the organism faces one or more physiological challenges. A "physiologically stressful state" may comprise pregnancy, lactation, or conditions in which an organism faces physiological challenges related to, for example, elevated metabolic demand, increased plasma volume, or decreased concentrations of nutrient-binding proteins. A "physiologically stressful state" may result from one or more disease states.

The term "subject," as used herein, comprises any and all organisms and includes the term "patient." "Subject" may refer to a human or any other animal. "Subject" may also refer to a fetus.

The phrase "pharmaceutically acceptable," as used herein, refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "swallowable form" refers to any compositions that do not readily dissolve when placed in the mouth and may be swallowed whole without any chewing or discomfort. In one embodiment, may have a shape containing no sharp edges and a smooth, uniform and substantially bubble free outer coating.

The phrase "co-administration" refers to administration of two compositions to a patient together or within a certain desired time.

The phrase "chewable form" refers to any relatively soft compositions that are chewed in the mouth after oral administration, have a pleasant taste and mouthfeel, and quickly break into smaller pieces and begin to dissolve after chewing such that they can be swallowed substantially as a solution.

The phrase "dissolvable form" refers to any compositions that dissolve into a solution in the mouth. Such compositions, in one embodiment, may dissolve within about 60 seconds or less after placement in the mouth without any chewing.

The term "mouthfeel" refers to non-taste-related aspects of the pleasantness experienced by a person while chewing or swallowing a nutritional supplement. Aspects of mouthfeel include, for example and without limitation, the hardness and brittleness of a composition, whether the composition is chewy, gritty, oily, creamy, watery, sticky, easily dissolved, astringent, effervescent, and the like, and the size, shape, and form of the composition (tablet, powder, gel, etc.).

The term "substantially free," as used herein, means free from therapeutically effective amounts of compounds when administered in suggested dosages, but may include trace amounts of compounds in non-therapeutically effective amounts. "Substantially free" may also mean including minimal amounts of compounds inadvertently and/or unintentionally introduced to the composition due to unavoidable constraints of the current state of the art; e.g., as contaminants or impurities in selected compounds.

As used herein, the terms "inactive," "inert," "excipient," and/or "formulatory" refer to any compound that is an inactive ingredient of a described composition. The definition of "inactive ingredient" as used herein follows that of the U.S. Food and Drug Administration, as defined in 21 C.F.R. 201.3 (b)(8), which is any component of a drug product other than the active ingredient. By "active ingredient," then, is meant any compound intended to furnish pharmacological activity or other direct effect in the diagnosis, cure, mitigation, treatment and/or prevention of a condition. See 21 C.F.R. 210.3 (b)(7). Further, "active ingredients" include those compounds of the composition that may undergo chemical change during the manufacture of the composition and be present in the final composition in a modified form intended to furnish an activity or effect. Id.

Proper nutrition is essential for maintaining health and preventing diseases. Adequate nutrition is especially critical during, for example, nutritionally volatile or physiologically stressful periods such as periods comprising, for example, pregnancy, lactation, or a disease state. Vitamin and mineral needs are almost universally increased throughout these periods. Such increased needs during physiologically stressful states, such as pregnancy or lactation, for example, may result from elevated metabolic demand, increased plasma volume, increased quantities of circulating red blood cells, decreased concentrations of nutrients, and/or decreased concentrations of nutrient-binding proteins such as, for example, serum-ferritin, maltose-binding protein, lactoferrin, calmodulin, tocopheryl binding protein, riboflavin binding protein, retinol binding protein, transthyretin, high density lipoprotein-apolipoprotein A1, folic acid binding protein, and 25-hydroxyvitamin D binding protein. Lapido, AMER J CLIN NUTR 72:280S-290S (Supp.) (2000).

Optimizing specific nutrients before, during, and after the physiological processes of pregnancy and lactation can have a profound, positive, and comprehensive impact on the overall wellness of the developing and newborn child, as well as the safety and health of the mother. Black, BRIT J NUTR 85:S193-197 (Supp.) (2001); Scholl et al., AMER J EPIDEM 146:134-141 (1997). Nutrients provided to a mother of course reach the fetus. Specifically, it is established that substrates for growth and development, for example, circulate within the same pathways that carry drugs to and waste products from the fetus. Exchanges of material between mother and fetus occur primarily in the placenta, where villi containing fetal capillaries protrude into sinuses (intervillous spaces). Maternal arterial blood flows into these spaces, then drains into maternal uterine veins to be returned to the maternal systemic circulation. Solutes in maternal blood cross the epithelial cells and connective tissue of the villi and the endothelium of the fetal capillaries; these solutes are then carried to the fetus by placental veins, which converge into the umbilical vein. THE MERCK MANUAL OF DIAGNOSIS AND THERAPY 17th ed., p. 2022, M H Beers and R B Berkow eds. (1999).

The methods and kits of the present invention provide the means to optimize good health by utilizing vitamin and mineral combinations for nutritional supplementation. The methods and kits of the present invention may be administered to or directed to a subject such as a human or any other organism.

The methods and kits of the present invention comprise compositions that may be co-administered. Co-administration of the compositions of the present invention and/or patient compliance may be found to achieve more effective nutritional supplementation, and thus better protect against disease and poor nutrition, and have a more positive and comprehensive impact upon the wellness of the developing and newborn child, and upon the safety and health of the mother.

The methods and kits of the present invention may comprise compounds comprising vitamin A. This vitamin functions in physiological processes resulting in cellular differentiation, cellular maturity, and cellular specificity. In this regard vitamin A is an important component of a nutritional supplement for subjects in a physiologically stressful state, such as pregnancy or lactation. Zile et al., J NUTR 131(3):705-08 (2001).

The compounds and methods of the present invention may comprise a particular form of vitamin A; for example, the pro-vitamin A carotenoid, beta carotene. Beta carotene is converted to vitamin A within the body as needed, thereby avoiding the risk of vitamin A toxicity. Mayne, FASEB J 10:690-701 (1996).

The novel compositions and methods of the present invention may comprise or use vitamin A, specifically in amounts ranging from about 1350 IU to about 4050 IU and, in a specific embodiment, around 2700 IU. The novel kits and methods of the present invention may be comprised of compositions comprising vitamin A, specifically in amounts of 0 IU, 2690 IU, 2691 IU, 2692 IU, 2693 IU, 2694 IU, 2695 IU, 2696 IU, 2697 IU, 2698 IU, 2699 IU, 2700 IU, 2701 IU, 2702 IU, 2703 IU, 2704 IU, 2705 IU, 2706 IU, 2707 IU, 2708 IU, 2709 IU or 2710 IU.

The methods and kits of the present invention may comprise compounds comprising vitamin D. Vitamin D is a fat-soluble "hormone like" substance important for the maintenance of healthy bones. This vitamin increases the absorption of calcium and phosphorous from the gastrointestinal tract, and improves mineral resorption into bone tissue. The result of this physiological function is a correlation between adequate systemic levels in pregnancy and a long-lasting reduction in osteoporotic fractures throughout the lifespan of the newborn. M F Holick, "Vitamin D," in MODERN NUTRITION IN HEALTH AND DISEASE, p. 313, M E Shils, J A Olsen and M. Shike eds., Plea and Febiger, Philadelphia, Penn. (1994); MK Javaid et al., LANCET 367(9504):36-43 (2006).

Vitamin D can be converted to its active form from exposure of the skin to sunlight. This fact is among the reasons why vitamin D deficiency is common in the elderly, notably the institutionalized, who spend little or no time out of doors.

Deficiencies lead to increased bone turnover and loss, and when severe, osteomalacia, or softening of the bones. Supplementation with vitamin D has been shown to moderately reduce bone loss, increase serum 25-hydroxyvitamin D, and decrease serum parathyroid hormone levels. Dawson-Hughes et al., NEW ENG J MED 337:670-76 (1997); Lips et al., J CLIN ENDOCRINOL METAB 86:1212-21 (2001).

The research findings into the essentiality of optimal vitamin D status during pregnancy and its implications, continue to expand far beyond bone health. Correlations include vitamin D's role in infant immunity, neurodevelopment, birth weight, and incidence of asthma. Growing research findings regarding the importance of this hormone-like compound is due, in large part, to the fact that vitamin D receptors have now been identified on nearly every tissue and cell in the human body. H F DeLuca et al., FASEB J 15:2579-2585 (2001); D. Eyles et al., NEUROSCIENCE 118(3):641-653 (2003); C A Mannion et al., CMAJ 174(9):1273-1277 (2006); B W Hollis et al., CMAJ 174(9):1287-1290 (2006); American Academy of Allergy, Asthma and Immunology Annual Meeting, Miami, Fl. (March 2006).

The vitamin D of the compositions and methods of the present invention may comprise vitamin $D_3$ (cholecalciferol). In the body, vitamin $D_3$ is produced when its precursor is exposed to ultraviolet irradiation (e.g., sunlight) and then hydroxylated in the liver to form 25-hydroxyvitamin $D_3$, a form of vitamin D in circulation. This form of the vitamin may be hydroxylated again in the kidney, yielding 1,25-hydroxyvitamin $D_3$, a potent form of vitamin D. Vitamin $D_3$ plays a role in the maintenance of calcium and phosphorus homeostasis, but it is also active in cell differentiation and immune function. The novel compositions and methods of the present invention may comprise or use vitamin D, specifically in amounts ranging from about 200 IU to about 600 IU and, in a specific embodiment, around 400 IU. The novel kits and methods of the present invention may be comprised of compositions comprising vitamin D, specifically in amounts of 0 IU, 390 IU, 391 IU, 392 IU, 393 IU, 394 IU, 395 IU, 396 IU, 397 IU, 398 IU, 399 IU, 400 IU, 401 IU, 402 IU, 403 IU, 404 IU, 405 IU, 406 IU, 407 IU, 408 IU, 409 IU or 410 IU.

The methods and kits of the present invention may comprise compounds comprising vitamin C (also known as ascorbic acid). Vitamin C, along with vitamin E, is a key antioxidant nutrient. The major biochemical role of the water-soluble vitamin C is as a co-substrate in metal catalyzed hydroxylations. Vitamin C also has antioxidant properties in interacting directly with superoxide hydroxyl radicals and singlet oxygen. Additionally, vitamin C provides antioxidant protection for folate and vitamin E, keeping vitamin E in its most potent form.

The damaging effects of a process known as oxidative stress, which includes free radical production and lipid peroxidation has been associated with over 200 disease processes. Rock et al., J AMER DIET ASSOC 96(7):693-702 (1996). The area of antioxidant research has extended into optimizing nutritional health during pregnancy. Specifically, lipid peroxidation may be implicated, for example, in the pathophysiology of preeclampsia, a toxemia of pregnancy. Antioxidant nutrients such as vitamin C may afford protective effects against preeclampsia by participating in the scavenging of free radicals. Indeed, significantly lower levels of vitamin C have been observed in preeclamptic women than in controls. Woods et al., AM J OBSTET GYNECOL 185(1):5-10 (2001); Kharb, EURO J OBSTET GYNECOL REPROD BIOL 1:37-39 (2000); Milczarek et al., MOL CELL BIOCHEM 210:65-73 (2000).

Vitamin C also enhances the absorption of iron. NATIONAL RESEARCH COUNCIL, RECOMMENDED DIETARY ALLOWANCES 115, 10th ed. (1989) (hereinafter "RDA"). In addition, vitamin C is required for collagen synthesis, epinephrine synthesis, and bile acid formation. Moreover, vitamin C has been implicated in inhibiting atherosclerosis by being present in extracellular fluid of the arterial wall and potentiating nitric oxide activity, thus normalizing vascular function. The novel compositions and methods of the present invention may comprise or use vitamin C, specifically in amounts ranging from about 35 mg to about 105 mg and, in a specific embodiment, around 70 mg. The novel kits and methods of the present invention may be comprised of compositions comprising vitamin C, specifically in amounts of 0 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg or 80 mg.

The methods and kits of the present invention may comprise compounds comprising vitamin E. Vitamin E is a fat-soluble vitamin antioxidant found in biological membranes where it protects the phospholipid membrane from oxidative stress. One form of vitamin E, dl-alpha-tocopheryl acetate (BASF Corporation, Mount Olive, N.J.), is used to fortify foods and pharmaceuticals and may be used within the context of the present invention. Vitamin E inhibits the oxidation of unsaturated fatty acids by trapping peroxyl free radicals. It is also an antiatherogenic agent, and studies have demonstrated a reduced risk of coronary heart disease with increased intake of vitamin E. Stampfer et al., NEW ENG J MED 328:1444-1449 (1993). In addition, vitamin E, like vitamin C, may afford protective effects against preeclampsia by participating in the scavenging of free radicals. Indeed, significantly lower levels of vitamin E have been observed in preeclamptic women than in controls. Woods et al., AM J OBSTET GYNECOL 185(1):5-10 (2001); Kharb, EURO J OBSTET GYNECOL REPROD BIOL 1:37-39 (2000); Milczarek et al., MOL CELL BIOCHEM 210:65-73 (2000).

The novel compositions and methods of the present invention may comprise or use vitamin E, specifically in amounts ranging from about 15 IU to about 45 IU and, in a specific embodiment, around 30 IU. The novel kits and methods of the present invention may be comprised of compositions comprising vitamin E, specifically in amounts of 0 IU, 20 IU, 21 IU, 22 IU, 23 IU, 24 IU, 25 IU, 26 IU, 27 IU, 28 IU, 29 IU, 30 IU, 31 IU, 32 IU, 33 IU, 34 IU, 35 IU, 36 IU, 37 IU, 38 IU, 39 IU or 40 IU.

The methods and kits of the present invention may comprise compounds comprising B-complex vitamins. This class of vitamins comprises the water-soluble nutrients not generally stored in the body to any great extent. The B-complex vitamins of the present compositions and methods may comprise one or more of thiamine ($B_1$), riboflavin ($B_2$), niacin ($B_3$), folic acid, pyridoxine ($B_6$) and cyanocobalamin ($B_{12}$). B-complex vitamins play roles in a variety of biological processes critical to the health of pregnant women, lactating women, and fetuses such as, for example, erythropoiesis (red blood cell production), and the metabolism of homocysteine and subsequent blood level reduction. M. DeFalco et al., CLIN EXP OBSTET GYNECOL 27 (3-4):188-190 (2000). Among the functions of the B-complex vitamins is helping the body utilize energy from foods that are ingested. With the increased caloric needs of pregnancy comes an increased need for these nutrients for adequate caloric utilization. T K Eskes, CLIN EXP OBSTET GYNECOL 27 (3-4):157-167 (2000); Y X Yang et al., BIOMED ENVIRON SCI 13(4):280-286 (2000).

The methods and kits of the present invention may comprise compounds comprising folic acid. Folic acid plays a key role in synthesizing genetic material during cell reproduction. In physiological state that require increased cell reproduction such as pregnancy, folic acid needs are concurrently increased. Failure to achieve adequate folate status during pregnancy increases the risk of birth defects. G J Locksmith and P. Duff, OBSTET GYNECOL 91:1027-1037 (1998).

Neural Tube Defects (NTD's) are a group of nervous system abnormalities caused by an interruption of the normal early development of the neural tube. When the lower end of the neural tube fails to close, a common defect known as spina bifida occurs. Spina bifida is accompanied by varying degrees of paralysis secondary to the condition's effect on the spinal cord. Id. The B-complex vitamin folic acid has the demonstrated ability to prevent neural tube defects (NTD's) such as spina bifida caused by disturbed homocysteine metabolism. Folic acid itself plays a role in the metabolic reduction of the amino acid intermediary homocysteine. Elevated homocysteine levels have been correlated with vascular dysfunction and heart disease. Recent research has expanded beyond this into a possible relationship between NTD's and elevated homocysteine levels. This observation arises secondary to apparent elevations of homocysteine levels in mothers of children born with NTD's. Vanderput et al., EXP BIOL MED 226(4):243-270 (2001); DeFalco et al., CLIN EXP OBSTET GYNECOL 27:188-90 (2000); Eskes, CLIN EXP OBSTET GYNECOL 27:157-67 (2000); Locksmith and Duff, OBSTET GYNECOL 91:1027-1034 (1998). This correlation may explain in part the protective effect of folate against neural tube defects. Further, folic acid is important for the formation of red and white blood cells within bone marrow and plays a role in heme formation. RDA at 150.

The novel compositions and methods of the present invention may comprise or use folic acid, specifically in amounts ranging from about 0.5 mg to about 1.5 mg and, in a specific embodiment, around 1.0 mg. The novel kits and methods of the present invention may be comprised of compositions comprising folic acid, specifically in amounts of 0 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg or 2.0 mg.

The methods and kits of the present invention may comprise compounds comprising vitamin $B_1$. This vitamin plays a role in carbohydrate metabolism and neural function. It is a coenzyme for the oxidative decarboxylation of alpha-ketoacids (e.g., alpha-ketoglutarate and pyruvate) and for transketolase which is a component of the pentose phosphate pathway. Folate deficiency and malnutrition inhibit the activity of thiamine. RDA at 123. Vitamin $B_1$ is available in forms known to those of skill in the art, including the form of thiamine mononitrate (BASF Corporation, Mount Olive, N.J.). The novel compositions and methods of the present invention may comprise or use vitamin $B_1$, specifically in amounts ranging from about 0.8 mg to about 2.4 mg and, in a specific embodiment, around 1.6 mg. The novel kits and methods of the present invention may be comprised of compositions comprising vitamin B1, specifically in amounts of 0 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, or 2.6 mg.

The methods and kits of the present invention may comprise compounds comprising vitamin $B_2$ (riboflavin). Riboflavin is a component of two flavin coenzymes, flavin mononucleotide (FMN) and flavin adenine dinucleotide (FAD). These flavoenzymes are involved in a number of oxidation-reduction reactions including the conversion of pyridoxine and niacin. RDA at 132. Flavoenzymes also play a role in a number of metabolic pathways such as amino acid deamination, purine degradation, and fatty acid oxidation and thus help to maintain carbohydrate, amino acid, and lipid metabolism. The novel compositions and methods of the present invention may comprise or use vitamin $B_2$, specifically in amounts ranging from about 0.9 mg to about 2.7 mg and, in a specific embodiment, around 1.8 mg. The novel kits and methods of the present invention may be comprised of compositions comprising vitamin B2, specifically in amounts of 0 mg, 0.8 mg, 0.9 mg, 1.0 mg, 1.1 mg, 1.2 mg, 1.3 mg, 1.4 mg, 1.5 mg, 1.6 mg, 1.8 mg, 1.9 mg, 2.0 mg, 2.1 mg, 2.2 mg, 2.3 mg, 2.4 mg, 2.5 mg, 2.6 mg, 2.7 mg, or 2.8 mg.

The methods and kits of the present invention may comprise compounds comprising vitamin $B_6$ (pyridoxine). The administration of pyridoxine may reduce the levels of homocysteine. Bostom et al., KIDNEY INT 49:147-152 (1996). The active forms of pyridoxine, pyridoxal-5'-phosphate (PLP) and pyridoxamine-5'-phosphate, are coenzymes for numerous enzymes and as such, are important for gluconeogenesis, niacin formation, and erythrocyte metabolism. RDA at 142-43. Pyridoxine is a coenzyme for both cystathionine synthase and cystathionase, enzymes that catalyze the formation of cysteine from methionine. Homocysteine is an intermediate in this process and elevated levels of plasma homocysteine are recognized as a risk factor for both vascular disease (Robinson et al., CIRCULATION 94:2743-2748 (1996)) and neural tube defects (Locksmith and Duff, OBSTET GYNECOL 91:1027-1034 (1998)). Vitamin $B_6$ is available in forms known to those of skill in the art, including the form of pyridoxine hydrochloride (BASF Corporation, Mount Olive, N.J.).

The novel compositions and methods of the present invention may comprise or use vitamin $B_6$, specifically in amounts ranging from about 1.25 mg to about 3.75 mg and, in a specific embodiment, around 2.5 mg. The novel kits and methods of the present invention may be comprised of compositions comprising vitamin B6, specifically in amounts of 0 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg or 3.5 mg.

The methods and kits of the present invention may comprise compounds comprising vitamin $B_{12}$. Cobalamin (a form of vitamin $B_{12}$) can be converted to the active coenzymes, methylcobalamin and 5'-deoxyadenosylcobalamin. These coenzymes are necessary for folic acid metabolism, conversion of coenzyme A, and myelin synthesis. For example, methylcobalamin catalyzes the demethylation of a folate cofactor which is involved in DNA synthesis. A lack of demethylation may result in folic acid deficiency. RDA at 159-60. Deoxyadenosylcobalamin is the coenzyme for the conversion of methylmalonyl-CoA to succinyl-CoA, which plays a role in the citric acid cycle. Importantly, cobalamin, along with pyridoxine and folic acid in implicated in the proper metabolism of homocysteine. Cobalamin is available as cyanocobalamin, methylcobalamin, hydroxocobalamin, adenosylcobalamin, and hydroxycyanocobalamin. The novel compositions and methods of the present invention may comprise or use vitamin $B_{12}$, specifically in amounts ranging from about 6 mcg to about 18 mcg and, in a specific embodiment, around 12 mcg. The novel kits and methods of the present invention may be comprised of compositions comprising vitamin B12, specifically in amounts of 0 mcg, 2 mcg, 3 mcg, 4 mcg, 5 mcg, 6 mcg, 7 mcg, 8 mcg, 9 mcg, 10 mcg, 11 mcg, 12 mcg, 13 mcg, 14 mcg, 15 mcg, 16 mcg, 17 mcg, 18 mcg, 19 mcg, 20 mcg, 21 mcg or 22 mcg.

The methods and kits of the present invention may comprise compounds comprising niacin. Niacin, also called vitamin $B_3$, is the common name for two compounds: nicotinic acid (also called niacin) and niacinamide (also called nicotinamide). Niacin is particularly important for maintaining healthy levels and types of fatty acids. Niacin is also required for the synthesis of pyroxidine, riboflavin, and folic acid. RDA at 137. Administration of niacin may also effect a reduction in total cholesterol (LDL) and very low density lipoprotein (VLDL) levels and an increase in high density lipoprotein (HDL) cholesterol levels. Nicotinamide adenine dinucleotide (NAD) and NAD phosphate (NADP) are active coenzymes of niacin. These coenzymes are involved in numerous enzymatic reactions such as glycolysis, fatty acid metabolism, and steroid synthesis. Henkin et al., AM J MED 91:239-246 (1991). The novel compositions and methods of the present invention may comprise or use niacin, specifically in amounts ranging from about 9 mg to about 27 mg and, in a specific embodiment, around 18 mg. The novel kits and methods of the present invention may be comprised of compositions comprising niacin, specifically in amounts of 0 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, or 28 mg.

Minerals are inorganic, or non-carbon-containing, elements that are critical for healthy physiological processes. Minerals are contemplated in the compositions of the kits and methods of the present invention. Such minerals may be in either chelated or non-chelated form. For example, minerals act as cofactors for hundreds of enzymes associated, for example, with food digestion, nucleic acid production, and protein synthesis. Minerals may also act as, for example, cofactors for antioxidant enzymes. The minerals of the compositions and methods of the present invention may comprise one or more of calcium, iron, magnesium, zinc, and copper.

The methods and kits of the present invention may comprise compounds comprising calcium in either chelated or non-chelated form. This mineral is required for proper functioning of numerous intracellular and extracellular processes including, for example, muscle contraction, nerve conduction, blood coagulation, and of particular interest in the context of pregnancy and lactation, hormone release. In addition, the calcium ion plays a unique role in intracellular signaling and is involved in the regulation of many enzymes. THE MERCK MANUAL OF DIAGNOSIS AND THERAPY 17th ed., p. 139, M H Beers and R. Berkow eds. (1999). Calcium is available in forms known to those of skill in the art, including the form of calcium carbonate, the active ingredient in TUMS® (GlaxoSmithKline, Research Triangle Park, NC). The novel compositions and methods of the present invention may comprise or use calcium, specifically in amounts ranging from about 50 mg to about 150 mg and, in a specific embodiment, around 100 mg. In addition, the novel compositions and methods of the present invention may comprise or use calcium in amounts of 0 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, or 110 mg.

The methods and kits of the present invention may comprise compounds comprising iron in either chelated or non-chelated form. Increased plasma volume and red blood cell number are among the reasons that the status of the essential mineral iron is critical during pregnancy. A primary function of iron is to carry oxygen to bodily tissues via the hemoglobin part of red blood cells. Supplemental intake of iron is critical to preventing anemia, a disorder associated with a variety of physiological states including, for example, pregnancy. Bothwell, AM J CLIN NUTR 72:257S-264S (Supp.) (2000). Anemia, or low iron status, is one of the most frequent complications related to pregnancy. Severe anemia may have adverse effects upon a mother and a fetus. Specifically, significant depression of hemoglobin has been associated with poor pregnancy outcome. Black, BRIT J NUTR 85:S193-197 (Supp. 2) (2001); Sifakis and Pharmakides, ANN NY ACAD SCI 900:125-136 (2000). The amounts of iron that can be absorbed, even from optimal diet, are less than the iron requirements in pregnancy. Supplemental iron is therefore recommended.

One form of iron known in the art is ferrous fumarate (Jost Chemical, St. Louis, Mo.). The novel compositions and methods of the present invention may comprise or use iron, specifically in amounts ranging from about 32.5 mg to about 97.5 mg and, in a specific embodiment, around 65 mg. In addition, the novel compositions and methods of the present invention may comprise or use iron in amounts of 0 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg.

The methods and kits of the present invention may comprise compounds comprising magnesium in either chelated or non-chelated form. Magnesium is important for over 300 different enzyme reactions. A primary function of magnesium is to bind to phosphate groups in adenosine triphosphate (ATP), thereby forming a complex that assists in the transfer of ATP phosphate. Magnesium also functions within cells as an allosteric activator of enzyme activity and for membrane stabilization. Magnesium also plays roles in nucleic acid synthesis, transcription of DNA and RNA, amino acid activation, and protein synthesis. ADVANCED NUTRITION AND HUMAN METABOLISM 2nd ed., p. 341, J L L Groff et al. eds. (1996).

Magnesium is found primarily in both bone and muscle. Magnesium is related to the reactions of over 300 enzymes, including enzymes associated with biosynthetic pathways, glycolysis, protein synthesis, transketolase reactions, and membrane transport. Magnesium is also involved in the formation of cAMP, a cytosolic second messenger that plays a role in cell signaling mechanisms. In addition, magnesium functions both synergistically and antagonistically with calcium in neuromuscular transmission. RDA at 188. Specifically, magnesium is critical for the maintenance of electrochemical potentials of nerve and muscle membranes and the neuromuscular junction transmissions, particularly important in the heart. Not surprisingly, magnesium deficiency is tied to cardiovascular disease and hypertension. Agus et al., CRIT CARE CLINICS 17:175-87 (2001). Indeed, oral magnesium therapy improves endothelial function in patients with coronary disease. Shechter et al., 102 CIRCULATION 2353-58 (2000). During pregnancy there is an obvious increase in cell replication and hence protein synthesis. These physiological processes require increased magnesium. MACROMINERALS IN ADVANCED NUTRITION AND HUMAN METABOLISM 2nd ed., pp. 325-351, J L Groff et al. eds., West Publishing Co., St. Paul, Minn. (1995).

Magnesium is available in a variety of salts. One form of magnesium known in the art is magnesium oxide (Mallinckrodt Baker, Inc., Phillipsburg, N.J.). The novel kits and methods of the present invention may be comprised of compositions comprising magnesium, specifically in amounts ranging from about 12.5 mg to about 37.5 mg and, in a specific embodiment, around 25 mg. The novel kits and methods of the present invention may be comprised of compositions comprising magnesium, specifically in amounts of 0 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg or 35 mg.

The methods and kits of the present invention may comprise compounds comprising zinc in either chelated or non-chelated form. Zinc plays a role in numerous metabolic activities. The increased need for zinc during pregnancy is largely attributed to its function in nucleic acid production in genetic material, protein synthesis, and development of the immune system. With the increase in cell growth and replication during the state of pregnancy, these functions are critical to a healthy pregnancy outcome. Common practices in pregnancy that, while necessary, can interfere with zinc absorption include the use of iron supplements and consumption of cereal-based foods high in dietary fiber. Zinc deficiencies in pregnancy have been shown to have an effect on fetal growth and, if severe, could cause severe fetal abnormalities. M. Srinivas et al., Indian J PEDIATR 68(6):519-22 (2001), J C King, AM J CLIN NUTR 71:1334S-1343S (2000), Y X Yang et al., BIOMED ENVIRON SCI 13(4):280-286 (2000).

There are more than 200 zinc metalloenzymes including aldolase, alcohol dehydrogenase, RNA polymerase, and protein kinase C. Zima et al., BLOOD PURIF 17:182-86 (1999). Zinc stabilizes RNA and DNA structures, forms zinc fingers in nuclear receptors, and is a component of chromatin proteins involved in transcription and replication. Zinc is available in many forms, such as zinc oxide (Reade Advanced Materials, Providence, R1) and zinc sulfate (United States Biological, Swampscott, Mass.). The novel compositions and methods of the present invention may comprise or use zinc, specifically in amounts ranging from about 12.5 mg to about 37.5 mg and, in a specific embodiment, around 25 mg. The novel kits and methods of the present invention may be comprised of compositions comprising zinc, specifically in amounts of 0 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg or 35 mg.

The methods and kits of the present invention may comprise compounds comprising copper in either chelated or non-chelated form. Copper is an important component of the process of gene expression. Additionally, one of copper's most vital roles is to help form hemoglobin, which, as previously discussed, carries oxygen to tissues via its iron component. In this respect copper plays a key role in protecting against anemia. Further, deficiencies of copper may lead to neutropenia and bone abnormalities in pregnant and lactating women. Uauy et al., AMER J CLIN NUTR 67:952S-959S (Supp.) (1998). In addition, a fetus must accumulate copper at a rate of 50 mcg×kg$^{-1}$×d$^{-1}$ over the latter half of pregnancy; any deficiency in accumulation may lead to low birth weight and protein-energy malnutrition. Id. Many forms of copper are known to those skilled in the art, including copper oxide (Reade Advanced Materials, Providence, R.I.). The novel compositions and methods of the present invention may comprise or use copper, specifically in amounts ranging from about 1 mg to about 3 mg and, in a specific embodiment, around 2.0 mg. The novel kits and methods of the present invention may be comprised of compositions comprising copper, specifically in amounts of 0 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, or 3.0 mg.

In a specific embodiment, vitamins and minerals that inhibit the benefits of the disclosed compounds comprising the nutritional supplements may be specifically excluded from the methods and kits of the present invention. Additionally, certain vitamins and minerals when taken in excess have been shown to have potentially negative physiological effects; certain of these vitamins and minerals may be specifically excluded from the methods and kits of this invention.

Chromium is a trace mineral essential for the human body. It is important in processing carbohydrates and fats, and helping the body respond to insulin. J B Vincent, PROC NUTR SOC 63(1):41-7 (2004). Chromium in the form of chromium picolinate is a popular nutritional supplement. However, intake of chromium picolinate bears some risks. Laboratory studies of chromium picolinate have shown that it reacts with antioxidants in cells to produce a reduced form of chromium, which is capable of causing DNA mutations. This mutagenic damaging of the cell's genetic material suggests that chromium picolinate could play a role in causing cancer. J B Vincent, SPORTS MED 33(3):213-30 (2003). In a specific embodiment, the methods and kits of the present invention may be free from added chromium.

Molybdenum is another trace mineral essential for the human body, which is commonly included in nutritional supplements. It has been shown to be required for maintaining normal growth in animals. PRESENT KNOWLEDGE IN NUTRITION 7th Ed., pp. 358-360, E E Ziegler and L J Filer, Jr. eds., ILSI Press, Washington, D.C. (1996). Excessively large oral doses, however, can create toxicity such as growth depression, anemia, and incidence of gout. Id. In a specific embodiment, the methods and kits of the present invention may be free from added molybdenum.

Care should also be taken to avoid an excess of vitamin A supplementation. Elevated serum levels of the active form of vitamin A, retinol, are correlated with increased bone fragility, with a resulting deleterious effect on bone health. Although retinol is involved in bone remodeling, excessive intake, as can occur with long-term supplementation at relatively high doses, has been linked to bone demineralization. Michaelson et al., N ENG J MED 348(4):287-294 (2003). In a specific embodiment, the methods and kits of the present invention may be free from added vitamin A.

Although iron is an essential nutrient with numerous functions, broad spectrum supplementation among the populous has come under scrutiny due to its role as a catalyst for oxidative stress. Day et al., 107 (20) CIRCULATION 2601-06 (2003). Oxidation, notably of Low-Density Lipoprotein (LDL) cholesterol, has been strongly correlated with an increased risk of cardiovascular disease. De Valk et al., 159 ARCH INT MED 1542-48 (1999). Accordingly, iron supplementation is indicated only in specific diagnostic states. In a specific embodiment, the methods and kits of the present invention may be free from added iron.

Although vitamin K, or phylloquinone, plays a role in the process of maintaining bone health, it also plays a major role in the synthesis of coagulation factors. This delicate balance of coagulation is at times purposefully altered in those with, or at high risk of, cardiovascular disease. Increased intake of vitamin K can alter the efficacy of specific medications used for this purpose. Further, the human body produces vitamin K from naturally occurring intestinal bacteria, thus making deficiency of this nutrient rare. Due to these factors, broad spectrum vitamin K supplementation is discouraged. Kurnik et al., ANN PHARMACOTHER 37(11):1603-06 (2003); Shearer, LANCET 345:229-34 (1995). In a specific embodiment, the methods and kits of the present invention may be free from added vitamin K.

Lactose is a disaccharide, or sugar that is found mainly in milk and dairy products. Lactose intolerance or the inability to properly digest and absorb this compound is relatively common. With this inability comes uncomfortable side effects such as abdominal bloating, pain, and diarrhea upon ingestion of lactose-containing foods. Since milk and dairy products are a primary source of both calcium and lactose, those who are lactose intolerant are more likely to have insufficient calcium intake and therefore osteoporosis. DiStefano et al., GASTROENTEROL 122(7):1793-99 (2002). In a specific embodiment, the methods and kits of the present invention may be free of added lactose.

Manganese is a trace element essential for adequate growth and reproduction, bone development and carbohydrate metabolism. PRESENT KNOWLEDGE IN NUTRITION 7th Ed., pp. 334-339, E E Ziegler and L J Filer, Jr. eds., ILSI Press, Washington, D.C. (1996). As such, it is commonly included in nutritional supplements. Manganese toxicity, however, is also recognized as a serious health hazard to humans, when the mineral is taken in excess doses. Id. This toxicity may result in severe abnormalities of the central nervous system. Id. Manganese toxicity has been reported in an individual who consumed high amounts of manganese supplements over an extended period of time, and individuals who consumed water containing high manganese concentrations. Id. In a specific embodiment, the methods and kits of the present invention may be free from added molybdenum.

In one embodiment of the present invention, specific vitamins and/or minerals of the first composition may be excluded. For example, in a specific embodiment, the first composition of the present invention may be substantially free of one or more of added vitamins and minerals selected from the group consisting of vitamin A, vitamin D, vitamin C, vitamin E, folic acid, vitamin $B_1$, vitamin $B_2$, vitamin $B_6$, vitamin $B_{12}$, niacin, calcium, iron, magnesium, zinc, and copper.

In another embodiment of the present invention, the compositions may be substantially free of other added active compounds, vitamins and/or coenzymes. In a specific embodiment, the compositions of the present invention may be substantially free of one or more of added compounds selected from the group consisting of lutein, lycopene, zeaxanthin, vitamin $B_4$, vitamin $B_5$, vitamin $B_7$, vitamin $B_8$, vitamin $B_{10}$, vitamin K, biotin, pantothenic acid, phosphorus, iodine, potassium, odorless garlic, coenzyme $Q_{10}$, 1-carnitine, grape seed extract, chloride, sodium, green tea extract, quercetin, fluoride, hawthorne berries, and alpha lipoic acid.

In another embodiment of the present invention, the compositions may be substantially free added minerals. In a specific embodiment the compositions of the present invention may be substantially free of one or more of added minerals selected from the group consisting of chromium, titanium, molybdenum, nickel, tin, silicon, vanadium, manganese, selenium, selenite, boron, bismuth, borax, bauxite, gold, silver, hydroxylapatite, mica, quartz, steatite, talc, sulfur, and zircon.

In another embodiment of the present invention, the compositions may be substantially free of added inactive compounds that serve merely as inert, excipient, and/or formulatory ingredients of the composition. In a specific embodiment, the compositions of the present invention may be substantially free of one or more of added compounds from the group consisting of magnesium stearate, silica, silicon dioxide, magnesium silicate, dicalcium phosphate, povidone, titanium dioxide, sodium benzoate, alpha lipoic acid, lutein, lycopene, cellulose, croscarmellose sodium, stearic acid, cellulose, hydroxylpropyl cellulose, hydroxypropyl methylcellulose, titanium dioxide, polydextrose, triacetin, dicalcium phosphate, polyethylene glycol, polyvinylpyrrolidone, mineral oil, methocel, sodium lauryl sulfate, and talc.

The kits and methods of the present invention may be comprised of a composition comprising a combination of vitamins and minerals, in either chelated or non-chelated form, that work together with various metabolic systems and physiological responses of the human body. The active ingredients are available from numerous commercial sources, and in several active forms or salts thereof, known to those of ordinary skill in the art. Hence, the compositions and methods of the present invention are not limited to comprising or using any particular form of the vitamin or mineral ingredient described herein.

Omega-3 fatty acids, also known as (n-3) fatty acids, are long-chain polyunsaturated fatty acids. Holub, CANADIAN MEDICAL ASSOCIATION JOURNAL 166:608-615 (2002). Omega-3 fatty acids are characterized as essential fatty acids (EFAs). Humans do not synthesize essential omega-3 fatty acids, and so are dependent upon dietary or supplemental sources for this nutrient. EFAs are required for the formation of a variety of eicosanoids, including prostaglandins, thromboxanes, prostacyclins, and leukotrienes. THE MERCK MANUAL 17th ed., pp. 2-3, 32-33 (1999). EFAs are needed for many physiologic processes including maintaining the integrity of the skin, maintaining the structure of cell membranes, and synthesizing prostaglandins and leukotrienes. Id.

Omega-3 fatty acids are important in cardiovascular care. Increasing the intake of omega-3 fatty acids through diet and supplementation results in a corresponding increase of these omega-3 fatty acids in tissue, cellular lipids, and circulatory lipids along with a simultaneous reduction in omega-6 fatty acids. See Holub supra. This fatty acid shift alters the physicochemical properties of cell membranes and their functioning, modifies cell signaling, gene expression and biosynthetic processes and eicosanoid formations. Id. This shift leads to beneficial cardiovascular effects. Benefits include decreased platelet adhesiveness and aggregation, overall reduction in thrombogenicity, antiatherogenic effects, lowered levels of blood triglycerides (elevated levels of triglycerides are linked with a progressively increased risk of ischemic heart disease), lowered blood pressure levels, reduction in arrhythmia, and a decreased the risk of coronary artery disease. Kirs-Etherton, CIRCULATION 106:2747-2757, 2002; See also THE MERCK MANUAL at 3; Holub supra.

The use of omega-3 fatty acids in dietary supplements specifically for women is suggested for counteracting breast cancer progression. B A Stoll, BR J NUTR 87(3):193-198 (2002). Long-chain omega-3 fatty acids consistently inhibit the growth of human breast cancer cells in culture and in animal models. Id.

Dietary intake of omega-3 fatty acids has also been positively correlated with neuropsychiatric health in several studies. G S Young, R Thomas et al., REPROD NUTR DEV 45:549-558, 2005. Societies with high levels of omega-3 fatty acids show lower rates of major depression (J R Hibbeln and N. Salem, AM J CLIN NUTR 62:1-9 (1995)), and bipolar disease (S. Noaghiul and J R Hibbeln, AM J PSYCHIATRY 160:2222-2227 (2003)). The omega-3 fatty acids are necessary to complete the development of the infant's brain, retina, and other organs including the skin. C A Francois, W E Connor et al., AM J CLIN NUTR 77:226-233, 2003.

Docahexaenoic acid (or docosahexaenoic acid, DHA), a major component of fish oil, is one example of an omega-3 fatty acid. Id. This omega-3 fatty acid has been shown to be of particular importance during pregnancy. Adequate DHA is vital for optimal fetal and infant brain/cognitive development, as well as for normal brain function throughout life. F M Rioux, O. Hernell et al., ACTA PAEDIATR 95(2):137-144 (2006). The sleep patterns of infants born to mothers with higher plasma phospholipid DHA suggest greater central nerve system maturity. S R Cheruku, C J Lammi-Keefe et al., AM J CLIN NUTR 76:608-613, 2002. Additionally, children with Attention Deficit Hyperactivity Disorder (ADHD) have been shown to have abnormal levels of DHA. E A Mitchell, M. Manku et al., CLIN PEDIATR 26:406-411 (1986); L J Stevens, J R Burgess et al., PHYSIOL BEHAV 59:915-920 (1996). Studies have indicated a correlation between maternal DHA intake and intelligence quotient in the child. The direct correlation between brain development and systemic DHA status is secondary to the fact that DHA is taken up by the brain in preference to other fatty acids. Adequate DHA levels in pregnancy have also been correlated with optimizing the length of gestation and decreasing the risk of neurodevelopmental psychopathology. These critical findings have prompted the National Institute of Health (NIH) to recommend that pregnant women consume at least 300 mg of omega-3 fatty acids during pregnancy. N. Neurenger et al., NUTR REV 44:285-294 (1986); G. Hornstra et al., AM J CLIN NUTR 71:285S-291S (2000); I B Helland et al., PEDIATRICS 111:E39-E44 (2003); F. Facchinetti et al., EUR REV MED PHARMACOL SCI 9(1):41-48 (2005); R K McNamara et al., PROSTAGLANDINS LEUKOT ESSENT FATTY ACIDS (29 Aug. 2006).

DHA is also important for the development of the infant retina and improving the visual acuity of the infant. C A Francois, W E Connor et al., AM J CLIN NUTR 77:226-233 (2003). Preterm infants have a more rapid development of visual acuity if fed human milk or formula enriched with DHA, compared to standard formula. M H Jorgensen, K F Michaelsen et al., LIPIDS 31(1):99-105 (1996). An increase in visual acuity has also been observed to develop more rapidly in term infants breast-fed from mothers whose diets are supplemented with DHA. Id.

In addition to the aforementioned benefit of DHA to the developing child, this essential fatty acid has also shown multiple health-promoting properties in adults. These include anti-thrombotic, anti-inflammatory and anti-atherosclerotic activity, all of which reduce the risk of heart disease. M Laidlaw and B J Holub, AM J CLIN NUTR 77:37-42 (2003). Inverse relationships have also been found between systemic levels of omega-3 fatty acids and incidence and severity of mood disorders and depression, including postpartum depression. Therefore, introduction of omega-3 during pregnancy has a double benefit, to both child and mother. F B Hu et al., JAMA 287(14):1815-1821 (2002); C. Von Schacky et al., ANN INTERN MED 130:554-562 (1999); G. Parker et al., AM J PSYCHIATRY 163(6):969-978 (2006); S J Otto et al., PROSTAGLANDINS LEUKOT ESSENT FATTY ACIDS 69(3):237-243 (2003).

For women, DHA is particularly useful in counteracting the progression of breast cancer. Human breast cancer cells exposed to DHA exhibit an increase in cell death by apoptosis. B A Stoll, BR J NUTR 87(3):193-198, 2002. DHA also inhibits cyclooxygenase-2, which promotes mammary carcinogenesis. Id. DHA supplementation during pregnancy has also been shown to increase the length of gestation by about six days, helping mothers carry to a healthy full term. C M Smuts et al., OBSTETRICS AND GYNECOLOGY 101(3):469-479 (2003).

Intake of omega-3 fatty acids such as DHA not only leads to their incorporation into cell membrane lipids (B A Stoll, BR J NUTR 87(3):193-198 (2002)), but also storage in adipose tissue and secretion in breast milk. C A Francois, W E Connor et al., AM J CLIN NUTR 77:226-233 (2003). Although the human body can derive a limited amount of DHA from another fatty acid known as alpha-linolenic acid, this process is inefficient for optimal needs. A rich dietary source of direct DHA is fish. Id. However, some lactating women are vegetarians, have limited access to fish or simply do not like fish. A further problem with encouraging increased fish intake in pregnancy is that most species contain methyl mercury (MeHg) in various amounts. MeHg is a potent neurotoxin that can increase the risk of retarded cognitive development. This concern prompted both the United States Environmental Protection Agency (2004) and the Food and Drug Administration (2001) to issue advisories recommending that pregnant women modify their fish consumption. These recommendations have resulted in a reduced intake of fish during pregnancy, thus helping to protect against fetal MeHg related harm. However, this has concurrently reduced maternal intake of DHA. In fact, a recent dietary study of over 100 pregnant or nursing women in the United States showed an astonishingly low intake of DHA on average (60-80 mg/day), and a dangerously low percentage (<2) consumed the aforementioned recommended intake of 300 mg/day of DHA as set forth by the NIH. J T Cohen et al., AM J PREV MED, 29:353-365 (2005); U.S. Department of Health and Human Services, U.S. Environmental Protection Agency, "What you need to know about mercury in fish and shellfish," Report EPA-823-F-04-009 (March 2004); E. Oken et al., OBSTET GYNECOL 102:346-351 (2003).

In these cases nutritional supplements would provide the DHA necessary for physiological benefits. Thus dietary supplementation of DHA to, e.g., a pregnant woman or nursing mother is a viable means of providing physiologically active DHA not only to the mother but also the infant.

DHA may be obtained in solid form, such as in a whole-cell microbial product, or in liquid form, such as in an oil. An example of DHA in oil form is DHASCO®-T vegetable oil from micro-algae (Martek Biosciences Corporation, Columbia, Md.). Modes of producing DHA, or food products or additives containing high concentrations of DHA, are known in the art. Some of these are described in U.S. Pat. Nos. 6,977,167; 5,407,957; 5,492,938; 5,340,594; 6,410,281; 6,451,567; 5,340,594; 6,607,900; 6,410,281; 6,451,567; and in U.S. Patent Application Publication Nos. 2003/0060509 A1; 2006/0099693 A1; 2005/0170479 A1; and 2006/0165735 A1, the disclosure of all of which are expressly incorporated by reference in their entireties.

In one embodiment, the methods and kits of the present invention may include omega-3 fatty acids such as DHA in amounts ranging from up to about 300 mg. In another embodiment, the methods and kits of the present invention may include omega-3 fatty acids such as DHA in amounts ranging from about 80 mg to about 120 mg. In yet another embodiment, the methods and kits of the present invention may include omega-3 fatty acids such as DHA in amounts ranging from about 90 mg to about 110 mg. In a specific embodiment, the methods and kits of the present invention may include omega-3 fatty acids such as DHA in an amount of about 100 mg.

Each of the active ingredient vitamins, minerals and fatty acids of the present invention is available from numerous commercial sources, and in several active forms or salts thereof, as known to those of ordinary skill in the art. Hence, the methods and kits of the present invention are not limited to comprising or using any particular form of the vitamin, mineral or fatty acid ingredient described herein. Each of the vitamins, minerals and fatty acids can be blended to form a single composition or can form multiple compositions, which may be co-administered.

Nutrition is a constantly evolving health science. Nearly as proliferative as research findings correlating nutrients and disease prevention are findings demonstrating that supplementation with some nutrients can be counter-productive to the health needs of specific populations. In a specific embodiment, the methods and kits of the present invention may be substantially free of other added vitamins, minerals, and coenzymes.

The compositions of the present invention are preferably administered in amounts sufficient to supplement the nutritional needs of individuals in physiologically stressful states, such as, for example, pregnancy, lactation, and any disease state.

A specific embodiment of the present invention may comprise swallowable compositions. Swallowable compositions are well known in the art and are those that do not readily dissolve when placed in the mouth and may be swallowed whole without any chewing or discomfort. In a specific embodiment of the present invention, the swallowable compositions may have a shape containing no sharp edges and a smooth, uniform and substantially bubble free outer coating.

A specific embodiment of the present invention may comprise swallowable compositions comprising vitamin A, vitamin D, vitamin C, vitamin E, folic acid, vitamin $B_1$, vitamin $B_2$, vitamin $B_6$, vitamin $B_{12}$, niacin, calcium, iron, magnesium, zinc, and copper, in caplet form. Another specific embodiment of the present invention may comprise swallowable compositions comprising omega-3 fatty acids such as DHA enclosed within a gel-cap. Another specific embodiment of the present invention may comprise compositions comprising omega-3 fatty acids such as DHA in liquid or oil form, in a bottle.

In another specific embodiment, the swallowable compositions of the present invention may be in the form of gel-caps. Gel-caps consist of a filler comprising one or more pharmaceutically active materials dissolved or dispersed in an appropriate liquid vehicle encapsulated in a gelatin shell generally comprising gelatin together with a plasticizer such as glycerin or sorbitol. The filler material may comprise, for example, polyethylene glycols. Gel-caps are well known to those of ordinary skill in the art. See for example, U.S. Pat. Nos. 4,780,316; 5,419,916; 5,641,512; and 6,589,536. If more than one caplet or gel-cap is used, each individual caplet or gel-cap may be identical to the other caplets or gel-caps, or each may contain only some of the ingredients of the composition, so that the combination of the different caplets or gel-caps comprises a composition of the present invention. Another exemplary dosage of the compositions of the present invention may consist of one or more lozenges, the composition of each lozenge preferably being identical to each other lozenge.

To prepare the swallowable compositions in caplet form, each of the active ingredients may be combined in intimate admixture with a suitable carrier according to conventional compounding techniques. The carrier may take a wide variety of forms depending upon the form of the preparation desired for administration; e.g., oral, sublingual, nasal, via topical patch, or parenteral. In a specific embodiment of swallowable compositions of the present invention, the surface of the compositions may be coated with a polymeric film. Such a film coating has several beneficial effects. First, it reduces the adhesion of the compositions to the inner surface of the mouth, thereby increasing the patient's ability to swallow the compositions. Second, the film may aid in masking the unpleasant taste of certain drugs. Third, the film coating may protect the compositions of the present invention from atmospheric degradation. Polymeric films that may be used in preparing the swallowable compositions of the present invention include vinyl polymers such as polyvinylpyrrolidone, polyvinyl alcohol and acetate, cellulosics such as methyl and ethyl cellulose, hydroxyethyl cellulose and hydroxylpropyl methylcellulose, acrylates and methacrylates, copolymers such as the vinyl-maleic acid and styrene-maleic acid types, and natural gums and resins such as zein, gelatin, shellac and acacia. Pharmaceutical carriers and formulations for swallowable compounds are well known to those of ordinary skill in the art. See generally, e.g., HANDBOOK OF PHARMACEUTICAL EXCIPIENTS 2nd ed., Wade and Waller eds. (1994).

A specific embodiment of the present invention may comprise swallowable compositions. Swallowable compositions are well known in the art and are those that do not readily dissolve when placed in the mouth and may be swallowed whole without any chewing or discomfort. In a specific embodiment of the present invention the swallowable compositions may have a shape containing no sharp edges and a smooth, uniform and substantially bubble free outer coating.

To prepare the swallowable compositions of the present invention, each of the active ingredients may be combined in intimate admixture with a suitable carrier according to conventional compounding techniques. In a specific embodiment of the swallowable compositions of the present invention, the surface of the compositions may be coated with a polymeric film. Such a film coating has several beneficial effects. First, it reduces the adhesion of the compositions to the inner surface of the mouth, thereby increasing the patient's ability to swallow the compositions. Second, the film may aid in masking the unpleasant taste of certain drugs. Third, the film coating may protect the compositions of the present invention from atmospheric degradation. Polymeric films that may be used in preparing the swallowable compositions of the present invention include vinyl polymers such as polyvinylpyrrolidone, polyvinyl alcohol and acetate, cellulosics such as methyl and ethyl cellulose, hydroxyethyl cellulose and hydroxylpropyl methylcellulose, acrylates and methacrylates, copolymers such as the vinyl-maleic acid and styrene-maleic acid types, and natural gums and resins such as zein, gelatin, shellac and acacia. Pharmaceutical carriers and formulations for swallowable compounds are well known to those of ordinary skill in the art. See generally, e.g., HANDBOOK OF PHARMACEUTICAL EXCIPIENTS 2nd ed., Wade and Waller eds. (1994).

In a specific embodiment of the present invention, the compositions may comprise chewable compositions. Chewable compositions are those that have a palatable taste and mouthfeel, are relatively soft and quickly break into smaller pieces and begin to dissolve after chewing such that they are swallowed substantially as a solution.

In order to create chewable compositions, certain ingredients should be included to achieve the attributes just described. For example, chewable compositions should include ingredients that create pleasant flavor and mouthfeel and promote relative softness and dissolvability in the mouth. The following discussion describes ingredients that may help to achieve these characteristics.

Chewable compositions preferably have a pleasant or palatable flavor. Palatable flavors may be achieved by including sweetening agents and/or flavorants. Sweetening agents that may be included in the compositions of the present invention include, by way of example and without limitation, sucrose, fructose, high fructose corn syrup, dextrose, saccharin sodium, maltodextrin, aspartame, potassium acesulfame, neohesperidin dihydrochalcone, sucralose, monoammonium glycyrrhizinate, and others known to those of ordinary skill in the art. As used herein, the term "flavorant" means natural or artificial compounds used to impart a pleasant flavor and often odor to a pharmaceutical preparation. Flavorants that may be used in the present invention include, for example and without limitation, natural and synthetic flavor oils, flavoring aromatics, extracts from plants, leaves, flowers, and fruits and combinations thereof. Such flavorants include, by way of example and without limitation, anise oil, cinnamon oil, vanilla, vanillin, cocoa, chocolate, natural chocolate flavor, menthol, grape, peppermint oil, oil of wintergreen, clove oil, bay oil, anise oil, eucalyptus, thyme oil, cedar leave oil, oil of nutmeg, oil of sage, oil of bitter almonds, cassia oil; citrus oils, such as lemon, orange, lime and grapefruit oils; and fruit essences, including apple, pear, peach, berry, wildberry, date, blueberry, kiwi, strawberry, raspberry, cherry, plum, pineapple, and apricot. All of these flavorants are commercially available. In a specific embodiment of the present invention, flavorants that may be used include natural berry extracts and natural mixed berry flavor, as well as citric and malic acid. The amount of flavorants used may depend on a number of factors, including desired taste characteristics. While not necessary, one or more of these sweetening agents and/or flavorants also may be included in the swallowable compositions of the present invention.

In addition to having a palatable flavor, chewable compositions also should have a pleasant mouthfeel. A variety of ingredients can be included in the compositions of the present invention to enhance mouthfeel.

In the chewable compositions of the present invention, sugars such as white sugar, corn syrup, sorbitol (solution), maltitol (syrup), oligosaccharide, isomaltooligosaccharide, sucrose, fructose, lactose, glucose, lycasin, xylitol, lactitol, erythritol, mannitol, isomaltose, dextrose, polydextrose, dextrin, compressible cellulose, compressible honey, compressible molasses and mixtures thereof may be added to improve mouthfeel and palatability. Further, by way of example and without limitation, fondant or gums such as gelatin, agar, arabic gum, guar gum, and carrageenan may be added to improve the chewiness of the compositions. Fatty materials that may be included in the present invention include, by way of example and without limitation, vegetable oils (including palm oil, palm hydrogenated oil, corn germ hydrogenated oil, castor hydrogenated oil, cotton-seed oil, olive oil, peanut oil, palm olein oil, and palm stearin oil), animal oils (including refined oil and refined lard whose melting point ranges from 30° to 42° C.), Cacao fat, margarine, butter, and shortening.

Alkyl polysiloxanes (commercially available polymers sold in a variety of molecular weight ranges and with a variety of different substitution patterns) also may be used in the present invention to enhance the texture, the mouthfeel, or both of the chewable nutritional supplement compositions described herein. By "enhance the texture" it is meant that the alkyl polysiloxane improves one or more of the stiffness, the brittleness, and the chewiness of the chewable supplement, relative to the same preparation lacking the alkyl polysiloxane. By "enhance the mouthfeel" it is meant that the alkyl polysiloxane reduces the gritty texture of the supplement once it has liquefied in the mouth, relative to the same preparation lacking the alkyl polysiloxane.

Alkyl polysiloxanes generally comprise a silicon and oxygen-containing polymeric backbone with one or more alkyl groups pending from the silicon atoms of the back bone. Depending upon their grade, they can further comprise silica gel. Alkyl polysiloxanes are generally viscous oils. Exemplary alkyl polysiloxanes that can be used in the swallowable, chewable or dissolvable compositions of the present invention include, by way of example and without limitation, monoalkyl or dialkyl polysiloxanes, wherein the alkyl group is independently selected at each occurrence from a $C_1$-$C_6$-alkyl group optionally substituted with a phenyl group. A specific alkyl polysiloxane that may be used is dimethyl polysiloxane (generally referred to as simethicone). More specifically, a granular simethicone preparation designated simethicone GS may be used. Simethicone GS is a preparation which contains 30% simethicone USP. Simethicone USP contains not less than about 90.5% by weight $(CH_3)_3$—Si$\{OSi(CH_3)_2\}CH_3$ in admixture with about 4.0% to about 7.0% by weight $SiO_2$.

To prevent the stickiness that can appear in conventional chewable compositions and to facilitate conversion of the active ingredients to emulsion or suspension upon taking, the compositions of the present invention, may further comprise emulsifiers such as, by way of example and without limitation, glycerin fatty acid ester, sorbitan monostearate, sucrose fatty acid ester, lecithin and mixtures thereof. In a specific embodiment, one or more of such emulsifiers may be present in an amount of about 0.01% to about 5.0%, by weight of the administered compositions. If the level of emulsifier is lower or higher than the said range, the emulsification cannot be realized, or wax value will rise.

Chewable compositions should begin to break and dissolve in the mouth shortly after chewing begins such that the compositions can be swallowed substantially as a solution. The dissolution profile of chewable compositions may be enhanced by including rapidly water-soluble fillers and excipients. Rapidly water-soluble fillers and excipients preferably dissolve within about 60 seconds of being wetted with saliva. Indeed, it is contemplated that if enough water-soluble excipients are included in the compositions of the present invention, they may become dissolvable rather than chewable composition forms. Examples of rapidly water soluble fillers suitable for use with the present invention include, by way of example and without limitation, saccharides, amino acids and the like. In a specific embodiment, the saccharide may be a mono-, di- or oligosaccharide. Examples of saccharides which may be added to the compositions of the present invention include, by way of example and without limitation, sorbitol, glucose, dextrose, fructose, maltose and xylitol (all monosaccharides); and sucrose, lactose, glucose, galactose and mannitol (all disaccharides). Other suitable saccharides are oligosaccharides. Examples of oligosaccharides are dextrates and maltodextrins. Other water soluble excipients that may be used with the present invention include, by way of example and without limitation, amino acids such as alanine, arginine, aspartic acid, asparagine, cysteine, glutamic acid, glutamine, glycine, histidine, isoleucine, leucine, lysine, methionine, phenylalanine, proline, serine, threonine, tryptophan, tyrosine and valine.

Disintegrants also may be included in the compositions of the present invention in order to facilitate dissolution. Disintegrants, including permeabilising and wicking agents, are capable of drawing water or saliva up into the compositions which promotes dissolution from the inside as well as the outside of the compositions. Such disintegrants, permeabilising and/or wicking agents that may be used in the present invention include by way of example and without limitation, starches such as corn starch, potato starch, pre-gelatinized and modified starches thereof, cellulosic agents such as Ac-di-sol, montmorrilonite clays, cross-linked PVP, sweeteners, bentonite, microcrystalline cellulose, croscarmellose sodium, alginates, sodium starch glycolate, gums such as agar, guar, locust bean, karaya, pectin, Arabic, xanthan and tragacanth, silica with a high affinity for aqueous solvents, such as colloidal silica, precipitated silica, maltodextrins, beta-cyclodextrins, polymers, such as carbopol, and cellulosic agents such as hydroxymethylcellulose, hydroxypropylcellulose and hydroxyopropylmethylcellulose.

Finally, dissolution of the compositions may be facilitated by including relatively small particle sizes of the ingredients used.

In addition to those described above, any appropriate fillers and excipients may be utilized in preparing the swallowable compositions of the present invention so long as they are consistent with the objectives described herein. For example, binders are substances used to cause adhesion of powder particles in granulations. Such compounds appropriate for use in the present invention include, by way of example and without limitation, acacia, compressible sugar, gelatin, sucrose and its derivatives, maltodextrin, cellulosic polymers, such as ethylcellulose, hydroxypropylcellulose, hydroxypropylmethyl cellulose, carboxymethylcellulose sodium, and methylcellulose, acrylic polymers, such as insoluble acrylate ammoniomethacrylate copolymer, polyacrylate or polymethacrylic copolymer, povidones, copovidones, polyvinylalcohols, alginic acid, sodium alginate, starch, pregelatinized starch, guar gum, polyethylene glycol, and others known to those of ordinary skill in the art.

Diluents also may be included in the compositions of the present invention in order to enhance the granulation of the compositions. Diluents can include, by way of example and without limitation, microcrystalline cellulose, sucrose, dicalcium phosphate, starches, and polyols of less than 13 carbon atoms, such as mannitol, xylitol, sorbitol, maltitol, and pharmaceutically acceptable amino acids, such as glycin, and their mixtures.

Lubricants are substances used in composition formulations that reduce friction during composition compression. Lubricants that may be used in the present invention include, by way of example and without limitation, stearic acid, calcium stearate, magnesium stearate, zinc stearate, talc, mineral and vegetable oils, benzoic acid, poly-(ethylene glycol), glyceryl behenate, stearyl fumarate, and others known to those of ordinary skill in the art.

Glidants improve the flow of powder blends during manufacturing and minimize composition weight variation. Glidants that may be used in the present invention include by way of example and without limitation, silicon dioxide, colloidal or fumed silica, magnesium stearate, calcium stearate, stearic acid, cornstarch, talc and others known to those of ordinary skill in the art.

Colorants also may be included in the nutritional supplement compositions of the present invention. As used herein, the term "colorant" includes compounds used to impart color to pharmaceutical preparations. Such compounds include, by way of example and without limitation, FD&C Red No. 3, FD&C Red No. 8, FD&C Red No. 20, FD&C Yellow No. 6, FD&C Blue No. 2, FD&C Green No. 5, FD&C Orange No. 5, caramel, and ferric oxide, red and others known to those of ordinary skill in the art. Coloring agents also can include pigments, dyes, tints, titanium dioxide, natural coloring agents such as grape skin extract, beet red powder, beta carotene, annato, carmine, turmeric, paprika, and others known to those of ordinary skill in the art. It is recognized that no colorant is required in the nutritional supplement compositions described herein.

If desired, compositions may be sugar coated or enteric coated by standard techniques.

The swallowable compositions of the present invention may be prepared using conventional methods and materials known in the pharmaceutical art. For example, U.S. Pat. Nos. 5,215,754 and 4,374,082 relate to methods for preparing swallowable compositions. Further, all pharmaceutical carriers and formulations described herein are well known to those of ordinary skill in the art, and determination of workable proportions in any particular instance will generally be within the capability of the person skilled in the art. Details concerning any of the excipients of the invention may be found in WADE & WALLER, supra. All active ingredients, fillers and excipients are commercially available from companies such as Aldrich Chemical Co., FMC Corp, Bayer, BASF, Alexi Fres, Witco, Mallinckrodt, Rhodia, ISP, and others.

A specific embodiment of the present invention may comprise swallowable compositions packaged in blister packs. Blister packs as packaging for swallowable compositions are well known to those of ordinary skill in the art. Blister packs may be made of a transparent plastic sheet which as been formed to carry a matrix of depression or blisters. One or more swallowable compositions are received in each depression or blister. A foil or plastic backing is then adhered across the plane of the sheet sealing the swallowable compositions in their respective blisters. Examples of materials used for the blister packs include, but are not limited to, aluminum, paper, polyester, PVC, and polypropylene. Alternative materials are known to those of ordinary skill in the art. To remove a swallowable composition, the depression material is pressed in and the composition is pushed through the backing material. Multiple blister packs may be placed in an outer package, often a box or carton for sale and distribution.

Another specific embodiment of the present invention may comprise swallowable compositions packaged in bottles. The bottle may be glass or plastic in form with a pop or screw top cap. Bottle packaging for compositions in swallowable form are well known to those of ordinary skill in the art.

Additionally, the unit dose forms may be individually wrapped, packaged as multiple units on paper strips or in vials of any size, without limitation. The swallowable, chewable or dissolvable compositions of the invention may be packaged in unit dose, rolls, bulk bottles, blister packs and combinations thereof, without limitation.

Other objectives, features and advantages of the present invention will become apparent from the following specific examples. The specific examples, while indicating specific embodiments of the invention, are provided by way of illustration only. Accordingly, the present invention also includes those various changes and modifications within the spirit and scope of the invention that may become apparent to those skilled in the art from this detailed description. The invention will be further illustrated by the following non-limiting examples.

EXAMPLES

Without requiring further elaboration, it is believed that one skilled in the art, using the preceding description, can utilize the present invention to the fullest extent. The following examples are illustrative only, and not limiting of the remainder of the disclosure in any way whatsoever.

Example 1

A first composition of the following formulation is prepared in caplet form, including the appropriate excipients, by standard methods known to those of ordinary skill in the art:

| | |
|---|---|
| Vitamin A (beta carotene) | 2700 IU |
| Vitamin D (cholecalciferol) | 400 IU |
| Vitamin C (ascorbic acid) | 70 mg |
| Vitamin E (dl-alpha-tocopheryl acetate) | 30 IU |
| Folic acid | 1.0 mg |
| Vitamin $B_1$ (thiamine mononitrate) | 1.6 mg |
| Vitamin $B_2$ (riboflavin) | 1.8 mg |
| Vitamin $B_6$ (pyridoxine hydrochloride) | 2.5 mg |
| Vitamin $B_{12}$ (cyanocobalamin) | 12 mcg |
| Niacin (niacinamide) | 18 mg |
| Calcium (calcium carbonate) | 100 mg |
| Iron (ferrous fumarate) | 65 mg |
| Magnesium (magnesium oxide) | 25 mg |
| Zinc (zinc oxide) | 25 mg |
| Copper (copper oxide) | 2.0 mg |

A second composition of the following formulation is prepared in gel-cap form by standard methods known to those of ordinary skill in the art:

| | |
|---|---|
| DHA, an omega-3 fatty acid | 100 mg |

Example 2

A study is undertaken to evaluate the effectiveness of the compositions of the present invention in the treatment of patients. The objective of the study is to determine whether oral intake of the compositions results in an improvement of the nutritional status of patients with regard to the specific vitamins and minerals contained in the administered compositions.

A double-blind, placebo controlled study is conducted over a six-month period. A total of 120 subjects (60 pregnant women entering the second trimester of pregnancy and 60 lactating women), aged 20-35 years, are chosen for the study. An initial assessment of the nutritional status of each woman is conducted. Vitamin A, beta carotene, niacin and vitamin $B_6$ are measured using high performance liquid chromatography. Erythrocyte transketolase activity is used to measure vitamin $B_1$ levels. Vitamin $B_2$ levels are determined by assessment of erythrocyte glutathione reductase activity. Vitamin $B_9$ is measured by radioimmunoassay (RIA), specifically The Solid Phase No Biol Folic Acid Kit (Diagnostic Products, Los Angeles, Calif.). Vitamin $B_{12}$ is measured by RIA using human intrinsic factor as a binder. Vitamin C levels are measured by spectrophotometric and colorimetric methods. Vitamin D is measured using an extraction double-antibody RIA (Dia Sorin, Inc., Stillwater, Minn.). Serum calcium is measured by the ionized calcium test. The peroxide hemolysis test is used to determine vitamin E status. Iron levels are measured using standard spectrophotometry. Similarly, magnesium levels are measured by absorbance of a magnesium chelate with xylidl blue at 660 nM. Zinc levels are assessed using flame atomic absorption spectrometry (Perkins Elmer 460, Norwalk, Conn.). Copper is measured by enzyme tests; either erythrocyte glutathione peroxidase or erythrocyte superoxide dismutase. DHA is measured and quantified using gas chromatography procedures.

Additionally, total serum homocysteine levels are determined by extraction on the Multi-Prep® gravity series GVSA-100 column, a strong anion exchange gravity flow column, and measurement by gas chromatography/mass spectrometry. Biochemical Diagnostics, Austin, Tex.

The 120 subjects are separated into four separate groups of 30 women. In a first group comprising only pregnant women and in a second group comprising only lactating women, each subject is co-administered one dosage form of the first composition and one dosage form of the second composition as described in Example 1, once a day. In a third group comprising only pregnant women and in a fourth group comprising only lactating women, each subject is co-administered two different placebo dosage forms, once a day. No other nutritional supplements are taken by the subjects during the assessment period.

An assessment of the nutritional status of each woman is conducted utilizing the methods described above at two-week intervals for a three month period. The data is evaluated using multiple linear regression analysis and a standard t-test. In each analysis, the baseline value of the outcome variable is included in the model as a covariant. Treatment by covariant interaction effects is tested by the method outlined by Weigel and Narvaez, CONTROLLED CLINICAL TRIALS 12:378-94 (1991). If there are no significant interaction effects, the interaction terms are removed from the model. The regression model assumptions of normality and homogeneity of variance of residuals are evaluated by inspection of the plots of residuals versus predicted values. Detection of the temporal onset of effects is done sequentially by testing for the presence of significant treatment effects at 1, 2, 3, 4, 5, and 6 months, proceeding to the earlier time in sequence only when significant effects have been identified at each later time period. Changes from the baseline within each group are evaluated using paired t-tests. In addition, analysis of variance is performed on all baseline measurements and measurable subject characteristics to assess homogeneity between groups. All statistical procedures are conducted using the Statistical Analysis System (SAS Institute Inc., Cary, N.C.). An alpha level of 0.05 is used in all statistical tests A statistically significant improvement in the nutritional status of vitamin, mineral, and DHA levels measured is observed in the treated subjects over the controls upon completion of the study. Homocysteine levels in women receiving supplements remain unelevated. Therefore, the study confirms that oral administration of the compositions of the present invention is effective in improving the nutritional status of patients. The length of gestation is increased by approximately six days in women receiving supplements, due to DHA intake, and their homocysteine levels are not elevated, due to folic acid intake, leading to a better prognosis regarding risk of neural tube defects in their infants.

While specific embodiments of the present invention have been described, other and further modifications and changes may be made without departing from the spirit of the invention. All further and other modifications and changes are included that come within the scope of the invention as set forth in the claims. The disclosure of each publication cited above is expressly incorporated by reference in its entirety to the same extent as if each were incorporated by reference individually.

What is claimed is:

1. A kit comprising a first composition consisting of vitamin A, vitamin D, vitamin C, vitamin E, folic acid, vitamin $B_1$, vitamin $B_2$, vitamin $B_6$, vitamin $B_{12}$, niacin, calcium, iron, magnesium, zinc, copper and one or more pharmaceutically acceptable carriers and a second composition consisting of omega-3 fatty acids and one or more pharmaceutically acceptable carriers.

2. The kit of claim 1 wherein said omega-3 fatty acids comprise docosahexaenoic acid (DHA).

3. The kit of claim 1 wherein said second composition comprises 250 mg DHA.

4. A The kit of claim 1 wherein said folic acid is provided in an amount of 1 mg.

5. The kit of claim 1 wherein said iron is ferrous fumarate.

6. The kit of claim 1 wherein said iron is provided in an amount of 65 mg.

7. The kit of claim 1 wherein said first composition consists of a caplet.

8. The kit of claim 7 wherein said caplet is film-coated.

9. The kit of claim 7 wherein said caplet is free of lactose, iodine and sugar.

10. The kit of claim of claim 1, wherein said folic acid comprises 5-methyl-(6S)-tetrahydrofolic acid or a pharmaceutically acceptable salt thereof.

11. The kit of claim 1, wherein said vitamin A comprises acetate.

12. The kit of claim 1, wherein said vitamin $B_1$ comprises thiamine mononitrate.

13. The kit of claim 1, wherein said vitamin $B_6$ comprises pyridoxine hydrochloride.

14. The kit of claim 1, wherein said folic acid comprises one or more natural derivatives of folate selected from the group consisting of (6S)-tetrahydrofolic acid or a polyglutamyl derivative thereof, 5-methyl-(6S)-tetrahydrofolic acid or a polyglutamyl derivative thereof, 5-formyl-(6S)-tetrahydrofolic acid or a polyglutamyl derivative thereof, 10-formyl-(6R)-tetrahydrofolic acid or a polyglutamyl derivative thereof, 5,10-methylene-(6R)-tetrahydrofolic acid or a polyglutamyl derivative thereof, 5,10-methenyl-(6R)-tetrahydrofolic acid or a polyglutamyl derivative thereof, and 5-formimino-(6S)-tetrahydrofolic acid or a polyglutamyl derivative thereof.

15. The kit of claim 1, wherein said vitamin $B_{12}$ comprises cyanocobalamin.

16. The kit of claim 1, wherein said vitamin C comprises ascorbic acid.

17. The kit of claim 1, wherein said vitamin E comprises d-alpha tocopheryl acetate.

18. The kit of claim 1, wherein said vitamin E comprises d-alpha tocopheryl succinate.

19. The kit of claim 1, wherein said magnesium comprises magnesium oxide.

20. The kit of claim 1, wherein said zinc comprises zinc oxide.

21. The kit of claim 1, wherein said kit provides nutritional supplementation for said patient during pregnancy patient is pregnant.

22. The kit of claim 1, wherein said kit provides nutritional supplementation for said patient that is lactating.

23. The kit of claim 1, wherein said omega-3 fatty acids are enclosed within a gel-cap.

24. The kit of claim 1, wherein said second composition is in liquid form.

25. The kit of claim 1, wherein said omega-3 fatty acids are present in the amount of up to about 300 mg and said first composition comprises about 2430 IU to about 2970 IU Vitamin A, about 360 IU to about 440 IU Vitamin D, about 63 mg to about 77 mg Vitamin C, about 27 IU to about 33 IU Vitamin E, about 0.9 mg to about 1.1 mg folic acid, about 1.44 mg to about 1.76 mg Vitamin B1, about 1.62 mg to about 1.98 mg Vitamin B2, about 2.25 mg to about 2.75 mg Vitamin B6, about 10.8 mcg to about 13.2 mcg Vitamin B12, about 16.2 mg to about 19.8 mg niacin, about 90 mg to about 110 mg calcium, about 58.5 mg to about 71.5 mg iron, about 22.5 mg to about 27.5 mg magnesium, about 22.5 mg to about 27.5 mg zinc, and about 1.8 mg to about 2.2 mg copper, wherein said first composition is free of any other added minerals and any other added vitamins.

26. The kit of claim 1, wherein said omega-3 fatty acids are present in the amount of about 250 mg and said first composition comprises about 2700 IU Vitamin A, about 400 IU Vitamin D, about 70 mg Vitamin C, about 30 IU Vitamin E, about 1 mg folic acid, about 1.6 mg Vitamin B1, about 1.8 mg Vitamin B2, about 2.5 mg Vitamin B6, about 12 mcg Vitamin B12, about 18 mg niacin, about 100 mg calcium, about 65 mg iron, about 25 mg magnesium, about 25 mg zinc, and about 2 mg copper, wherein said first composition is free of any other added minerals and any other added vitamins.

* * * * *